United States Patent
Su

(10) Patent No.: US 9,309,171 B2
(45) Date of Patent: *Apr. 12, 2016

(54) PROCESS FOR RECOVERING OLEFINS FROM MANUFACTURING OPERATIONS

(71) Applicant: Paul Su, Saratoga, CA (US)

(72) Inventor: Paul Su, Saratoga, CA (US)

(73) Assignee: Membrane Technology and Research, Inc., Newark, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/789,166

(22) Filed: Jul. 1, 2015

(65) Prior Publication Data

US 2016/0075620 A1 Mar. 17, 2016

Related U.S. Application Data

(63) Continuation-in-part of application No. 14/486,382, filed on Sep. 15, 2014, now Pat. No. 9,073,808.

(51) Int. Cl.
| | |
|---|---|
| C07C 7/144 | (2006.01) |
| C07C 7/09 | (2006.01) |
| C07C 7/00 | (2006.01) |

(52) U.S. Cl.
CPC ............. *C07C 7/144* (2013.01); *C07C 7/005* (2013.01); *C07C 7/09* (2013.01)

(58) Field of Classification Search
None
See application file for complete search history.

(56) References Cited

U.S. PATENT DOCUMENTS

| | | | |
|---|---|---|---|
| 4,623,704 A | 11/1986 | Dembicki et al. | |
| 5,089,033 A | 2/1992 | Wijmans | |
| 5,199,962 A | 4/1993 | Wijmans | |
| 5,769,927 A | 6/1998 | Gottschlich et al. | |
| 5,817,841 A | 10/1998 | Baker et al. | |
| 5,980,609 A | 11/1999 | Baker et al. | |
| 6,018,060 A | 1/2000 | Baker et al. | |
| 6,118,021 A | 9/2000 | Gottschlich et al. | |
| 6,271,319 B1 | 8/2001 | Baker et al. | |
| 6,414,202 B1 | 7/2002 | Baker et al. | |
| 6,428,606 B1 | 8/2002 | Gottschlich et al. | |
| 6,525,236 B1 | 2/2003 | Baker et al. | |
| 7,479,227 B2* | 1/2009 | Da Costa et al. | 210/640 |
| 8,309,776 B2 | 11/2012 | van Egmond et al. | |
| 2004/0173529 A1 | 9/2004 | Da Costa et al. | |
| 2005/0154247 A1 | 7/2005 | Jong et al. | |
| 2007/0232847 A1* | 10/2007 | Minhas et al. | 585/818 |
| 2011/0077446 A1* | 3/2011 | Shanbhag et al. | 585/818 |
| 2013/0303819 A1 | 11/2013 | Su | |
| 2014/0249339 A1* | 9/2014 | Simanzhenkov et al. | 585/252 |

OTHER PUBLICATIONS

Handbook of Petrochemicals and Processes, G.M. Wells, Gower Publishing, 1995.

* cited by examiner

*Primary Examiner* — Tam M Nguyen
(74) *Attorney, Agent, or Firm* — Timothy A. Hott; Janet Farrant

(57) ABSTRACT

A process for treating an effluent gas stream arising from a manufacturing operation that produces an olefin or a non-polymeric olefin derivative. The process involves cooling and condensing the effluent gas stream, which comprises an olefin, a paraffin, and a third gas, to produce a liquid condensate and an uncondensed (residual) gas stream. Both streams are then passed through membrane separation steps. The membrane separation of the uncondensed gas stream results in an olefin-enriched stream and an olefin-depleted stream. The olefin-enriched stream is recirculated within the process prior to the condensation step. The membrane separation of the condensate also results in an olefin-enriched stream, which may be recycled for use within the manufacturing operation, and an olefin-depleted stream, which may be purged from the process.

33 Claims, 11 Drawing Sheets

PROCESS FOR RECOVERING OLEFINS FROM MANUFACTURING OPERATIONS

CROSS-REFERENCE TO RELATED APPLICATIONS

This application is a continuation-in-part of U.S. application Ser. No. 14/486,382, filed Sep. 15, 2014, which issued Jul. 7, 2015 as U.S. Pat. No. 9,073,808 the disclosure of which is hereby incorporated herein by reference in its entirety.

FIELD OF THE INVENTION

The invention relates to a process for recovering olefins from a manufacturing operation. More specifically, the invention relates to treating an effluent gas stream using separation membranes for recovering olefin and separating paraffin.

BACKGROUND OF THE INVENTION

Olefins, such as ethylene and propylene, and their non-polymeric derivatives, such as isopropyl alcohol and cumene, account for some of the most demanded chemicals in the world. For example, the United States alone produces more than 10 billion pounds of chemicals derived from propylene annually.

Olefins are commonly produced by cracking hydrocarbon feedstocks or catalytically converting oxygenate feedstocks. Traditional methods for cracking include steam cracking, whereby naphtha or other hydrocarbons are reacted with steam to make light olefins, and fluid catalytic cracking (FCC), which is the refinery operation that breaks down larger hydrocarbons to produce naphtha-light components for gasoline, as well as olefins and heating oils. The conventional conversion of oxygenate feedstocks includes methanol-to-olefin (MTO) and methanol-to-propylene (MTP) processes. In MTO, methanol is converted primarily to ethylene and propylene in the presence of a molecular sieve catalyst. In MTP, methanol is dehydrated to produce dimethyl ether, which is then converted to propylene. Both processes involve complex operations downstream of the reactor(s) to purify the product, capture unconverted reagents for recycle, and purge contaminants. Typically, low temperature partial condensation is involved, and at least a portion of the uncondensed gas is recycled in the process.

In non-polymeric olefin derivative manufacturing, an olefin and other reagents are introduced into a high-pressure reactor. The raw effluent from the reactor is transferred continuously to one or more separation steps, from which a stream of raw derivative product is withdrawn for further purification. A stream of overhead gases, containing unreacted olefin, is also withdrawn from the separation steps and is recirculated back to the reactor.

Both of these types of manufacturing operations need to vent a portion of uncondensed gas to prevent build-up of unwanted contaminants in the reaction loop. However, the vented overhead gas typically contains unreacted olefin that, without further treatment, would otherwise go to waste.

Various process and techniques have been proposed for mitigating the loss of unreacted olefin in a variety of streams.

U.S. Pat. No. 4,623,704, to Dembicki et al. (Dow Chemical Company), discloses a process for treating a polymerization vent gas with a membrane. The vent stream is compressed and then cooled and condensed. Cooled gas and liquid are sent to a liquid/gas separator. After separation, the gas stream is sent through a series of membrane separation steps, which produce a permeate stream enriched in ethylene. The recovered ethylene is recycled to the polymerization process.

Co-owned U.S. Pat. Nos. 5,089,033 and 5,199,962, to Wijmans (Membrane Technology and Research, Inc.), disclose processes for recovering a condensable component in a gas stream that would otherwise be discharged into the atmosphere. The processes involve a condensation step and a membrane separation step. In one embodiment, the gas stream is compressed and cooled to carry out the condensation step. Uncondensed gas is then passed across a membrane that is selectively permeable to the condensable component.

Co-owned U.S. Pat. No. 6,271,319, to Baker et al. (Membrane Technology and Research, Inc.), discloses a process for treating the uncondensed gas stream using a gas separation membrane that is permeable for propylene over propane. A permeate stream enriched in olefin is withdrawn and recycled to the reactor inlet.

These patents, and other prior art technologies, have mainly focused on condensing a gas stream and recovering unreacted olefin from the resulting uncondensed gas produced from the condensation step. However, little is taught on recovering unreacted olefins from the condensed liquid stream.

Co-owned U.S. Pat. No. 5,769,927, to Gottschlich et al. (Membrane Technology and Research, Inc.), discloses a process for treating a purge vent stream from a polymer manufacturing operation. The purge vent stream contains an unreacted olefin monomer and nitrogen. The purge vent stream is initially treated in a condensation step. The uncondensed gas is then passed to a membrane separation step, where the membrane is organic-selective, meaning that the membrane is selective for unreacted monomer over other gases. The liquid condensate is directed to a flash evaporation step. The flashing step produces a liquid product stream enriched in monomer and a flash gas that is recirculated in the process.

Despite the above improvements, there remains a need for better olefin recovery technology applicable to processes that make or use olefins.

SUMMARY OF THE INVENTION

Accordingly, the present invention relates to a process for recovering olefins by treating an effluent gas stream comprising an olefin, a paraffin, and a third gas. The effluent stream is withdrawn from either an olefin or a non-polymeric olefin derivative manufacturing operation. During treatment, the effluent gas stream is condensed and separated, producing a liquid condensate stream and an uncondensed gas stream. Both of these streams contain olefin along with other components, such as paraffin and a third gas. To recover the unreacted olefin, both streams are treated by membrane separation steps. From treating the uncondensed gas stream, the olefin recovered is recycled back into the process upstream of the condensation step. Recovered unreacted olefin from treating the condensate may be sent in a recycle loop for use as feedstock back in the manufacturing operation.

Therefore, in a basic embodiment, the process of the invention includes the following steps:
 (a) passing an effluent gas stream to a compressor to produce a compressed stream;
 (b) partially condensing the compressed stream, including cooling and separating the compressed stream into a condensed liquid condensate enriched in olefin and paraffin and an uncondensed (residual) gas stream depleted in olefin and paraffin relative to the compressed stream;

(c) separating the condensed liquid condensate from step (b) using a first membrane to produce a first olefin-enriched permeate stream and a first olefin-depleted residue stream;

(d) separating the uncondensed gas stream from step (b) using a second membrane to produce a second olefin-enriched permeate stream and a second olefin-depleted residue stream; and (e) returning the second olefin-enriched permeate stream upstream of the compressor.

The effluent gas stream of step (a) may arise from two types of manufacturing operations. The first type is an operation that produces olefins. These operations include, but are not limited to, fluid catalytic cracking, olefin cracking, steam cracking, olefin metathesis, a methanol-to-olefin process (MTO), and a methanol-to-propylene (MTP) process. The second type is an operation that manufactures a non-polymeric olefin derivative, using olefins as a feedstock. Non-limiting examples of these operations include chlorohydrin production, butyraldehyde production, oxo alcohol production, isopropyl alcohol production, acrylic acid production, allyl chloride production, allyl alcohol production, acrylonitrile production, cumene production, ethylene oxide production, vinyl acetate production, ethylene dichloride production, ethanol production, and ethylbenzene production.

The effluent gas stream comprises an olefin, an analogous paraffin, and a third gas. In certain embodiments, the olefin is ethylene or propylene. In other embodiments, the olefin is butylene. The effluent gas stream may also comprise multiple sets of olefins and analogous paraffins, for example, ethane/ethylene and propane/propylene. The effluent gas stream also contains a third gas, such as hydrogen, nitrogen, or a non-polymeric olefin-derivative, such as cumene.

The goal of steps (a) and (b) is to bring the effluent gas stream to a pressure/temperature condition beyond the dewpoint of the olefin to be recovered, so that a portion of the olefin will condense out of the gas stream. Thus, the separation of the compressed stream creates a liquid condensate and an uncondensed (residual) gas stream. The condensate is enriched in olefin and paraffin and the uncondensed gas stream depleted in olefin and paraffin relative to the effluent stream.

The condensation step usually involves chilling and compression. Compressing the gas raises the dewpoint temperature, so a combination of compression and chilling is generally preferred.

In step (c), the liquid condensate from condensation step (b) is treated in a membrane separation step, which may be carried out under pervaporation or vapor permeation conditions. The membrane in this step is selective for olefin over paraffin. The membrane separation of step (c) thus results in a first permeate stream enriched in olefin and a first residue stream depleted in olefin.

In certain embodiments, the permeate stream enriched in olefin from step (c) is directed as a coolant stream to the condensation train.

Membranes for use in step (c) of the process of the invention may comprise any material suitable for preferentially permeating olefin over paraffin. In certain embodiments, the membrane preferably exhibits an olefin permeance of at least 400 gpu.

Step (c) may take the form of a single membrane separation operation or of multiple sub-operations, depending on the feed composition, membrane properties, and desired results.

In step (d), the uncondensed gas stream from condensation step (b) is passed as a feed stream and treated in a second membrane separation step. The membranes in step (d) are selectively permeable to olefins over paraffins and inorganic gases. A second permeate stream enriched in olefins and a second residue stream depleted in olefins are withdrawn from the membrane.

In step (e), the permeate stream from step (d) is recycled upstream of the compressor of step (a).

In a further embodiment, the process described above may be used to further separate the uncondensed gas stream. The olefin-depleted residue stream from step (d) is passed through an additional membrane separation step to produce a third olefin-enriched permeate and a third olefin-depleted residue stream. The membrane used in this step may be any material suitable for selectively permeating olefin over paraffin and other gases. Thus, in certain embodiments, the process comprises the steps (a)-(e), above, and the additional step of:

(f) separating the second olefin-depleted residue stream from step (d) using a third membrane to produce a third olefin-enriched permeate stream and a third olefin-depleted residue stream.

In certain embodiments, the process described above may also be used to further treat the liquid condensate stream by incorporating a further membrane separation step. The first olefin-depleted residue stream from step (c) is passed through an additional membrane separation step to produce a fourth olefin-enriched permeate stream and a fourth olefin-depleted residue stream. The fourth olefin-enriched permeate stream may then be recycled upstream of the compression step. Thus, in certain embodiments, the process comprises the steps (a)-(f), above, and the additional steps of:

(g) separating the first paraffin-enriched residue stream using a fourth membrane to produce a fourth olefin-enriched permeate stream and a fourth olefin-depleted residue stream; and (h) returning the fourth olefin-enriched permeate stream upstream of the compressor.

If the membrane separation of the condensate stream is to be carried out in the vapor phase, then the condensate stream must first be vaporized prior to step (c), such as by increasing the temperature or decreasing the pressure.

In a further embodiment, a membrane separation step may be performed to purify an additional gas in the effluent gas stream, such as hydrogen. Therefore, in certain embodiments, the process comprises the steps of:

(a) passing the feed gas stream to a compressor to produce a compressed stream;

(b) partially condensing the compressed stream, including cooling and separating the compressed stream into a condensed liquid condensate enriched in olefin and paraffin and an uncondensed (residual) gas stream depleted in olefin and paraffin relative to the compressed stream;

(c) separating the condensed liquid condensate from step (b) using a first membrane to produce an olefin-enriched permeate stream and an olefin-depleted residue stream;

(d) separating the uncondensed gas stream from step (b) using a second membrane to produce a hydrogen-enriched permeate stream and a hydrogen-depleted residue stream;

(e) separating the hydrogen-depleted residue from step (d) using a third membrane to produce a hydrocarbon-enriched permeate stream and a hydrocarbon-depleted residue stream; and (f) returning the hydrocarbon-enriched residue stream upstream of the compressor.

Occasionally, the conditions of the process may be such that the effluent gas stream is already at high pressure. In this case, chilling alone may suffice to induce condensation, and the compression step may be dispensed with. Thus, in yet another embodiment, the process comprises the steps of:
- (a) partially condensing the effluent gas stream, including cooling and separating the gas stream into a condensed liquid condensate enriched in olefin and paraffin and an uncondensed gas stream depleted in olefin and paraffin;
- (b) separating the condensed liquid condensate from step (a) using a first membrane to produce a first olefin-enriched permeate stream and a first olefin-depleted residue stream;
- (c) separating the uncondensed gas stream from step (a) using a second membrane to produce a second olefin-enriched permeate stream and a olefin-depleted residue stream;
- (d) passing the second olefin-enriched permeate stream to a compressor to produce a compressed stream; and
- (e) returning the compressed stream upstream of step (a).

Also disclosed herein is an apparatus for treating an effluent gas stream arising from an operation that manufactures olefins or non-polymeric olefin derivatives. The apparatus is designed to perform the processes of the invention. In a basic embodiment, the apparatus comprises the following components:
- (a) a compressor having an effluent gas inlet and a compressed gas outlet;
- (b) a condenser having a compressed gas inlet and a cooled gas outlet, wherein the compressed gas outlet of the compressor is in gas communication with the compressed gas inlet;
- (c) a phase separator having a cooled gas inlet, an uncondensed gas outlet, and a condensed gas outlet, wherein the cooled gas outlet of the condenser is in fluid communication with the cooled gas inlet;
- (d) a first separation unit having a first feed inlet, a first residue outlet, and a first permeate outlet, wherein the condensed gas outlet is in fluid communication with the first feed inlet; and
- (e) a second separation unit having a second feed inlet, a second residue outlet, and a second permeate outlet, wherein the uncondensed gas outlet is in gas communication with the second feed inlet, and wherein the second permeate outlet is in gas communication with the effluent gas inlet of the compressor.

In some embodiments, the apparatus may also include a vaporizer unit when the first separation unit operates under vapor permeation conditions. In other embodiments, where the effluent gas stream is already at high pressure, the compressor may be in gas communication with the second permeate outlet to compress the second permeate stream.

It is to be understood that the above summary and the following detailed description are intended to explain and illustrate the invention without restricting it in scope.

DETAILED DESCRIPTION OF THE INVENTION

Figure 1:
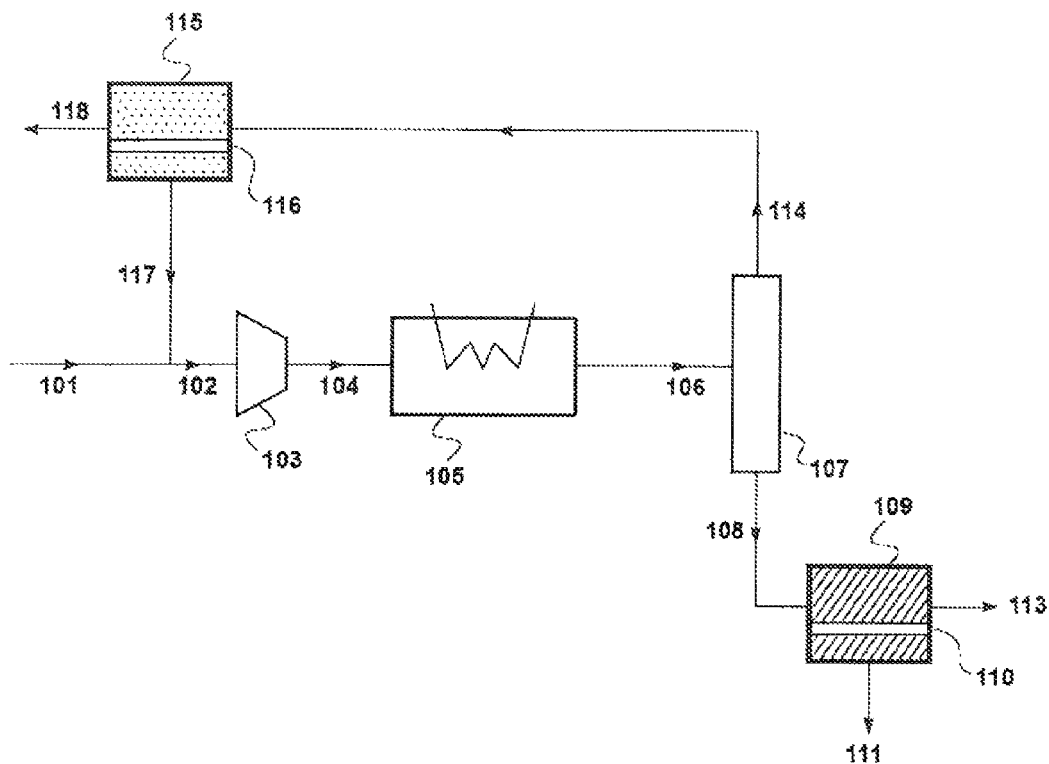
FIG. 1 is a schematic drawing showing an olefin recovery process comprising two membrane separation steps according to a basic embodiment of the invention.

The term "effluent gas stream" as used herein is construed as including a gas stream withdrawn from any unit operation or operations during an olefin or a non-polymer olefin-derivative manufacturing operation. That is, the effluent gas stream is not a stream withdrawn from a polymer manufacturing operation.

The term "olefin" as used herein means a member of the family of unsaturated hydrocarbons having a carbon-carbon double bond of the series $C_nH_{2n}$, including members in which at least one halogen atom has been substituted for one of the hydrogen atoms.

The term "non-polymeric olefin derivative" as used herein refers to a product made from at least one olefin, wherein the product does not contain repeating units of the olefin derivative monomer. Examples of propylene derivatives include, but are not limited to, chlorohydrin (a precursor of propylene oxide); butyraldehyde (a precursor to butyl alcohol); oxo alcohols, such as 2-methyl-2-butanol, n-butanol, 2-ethylhexanol, isononyl alcohol, and isodecyl alcohol; isopropyl alcohol; acrylic acid; allyl chloride; acrylonitrile; and cumene. Examples of ethylene derivatives include, but are not limited to, ethylene oxide, vinyl acetate, ethylene dichloride, ethanol, and ethylbenzene.

The term "$C_{2+}$ hydrocarbon" means a hydrocarbon having at least two carbon atoms.

The invention relates to an improved process for recovering unreacted olefin from an effluent gas stream, comprising an olefin, a paraffin, and a third gas that arises from olefin and olefin-derivative manufacturing operations. The process also provides for selectively purging paraffin from the reactor loop. By a reactor loop, we mean a configuration in which at least a part of the effluent gas stream from the reactor is recirculated directly or indirectly to the reactor. The process can be applied to any loop in which olefin is fed to the reactor, and in which olefin and paraffin are present in the effluent gas steam from the reaction loop.

In the embodiments described below, the effluent gas stream is withdrawn from either a manufacturing operation that produces olefins or a manufacturing operation that uses olefins as a feedstock to produce non-polymeric olefin-derivatives.

Such non-limiting examples of processes that produce olefins include fluid catalytic cracking, olefin cracking, steam cracking, olefin metathesis, a methanol-to-olefin process (MTO), and a methanol-to-propylene (MTP) process. A reference that provides discussion of design and operation of modern FCC units, a typical source of low-molecular weight olefins, is described in Chapter 3 of "Handbook of Petroleum Refining Processes" Second Edition, R. A. Meyers (Ed), McGraw Hill, 1997, incorporated by reference herein. The other processes are well known in the art and do not require any lengthy description herein.

For olefin-derivative manufacturing processes, non-limiting examples include the production of chlorohydrin (a precursor of propylene oxide), butyraldehyde (a precursor of butyl alcohol), isopropyl alcohol, acrylic acid, allyl chloride, acrylonitrile, cumene, ethylene oxide, vinyl acetate, ethylene dichloride, ethanol, and ethylbenzene.

It will be appreciated by those of skill in the art that FIG. 1 and the other figures showing process schemes herein are very simple block diagrams, intended to make clear the key unit operations of the embodiment processes of the invention, and that actual process trains may include many additional steps of standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from process to process.

A basic embodiment of the olefin recovery process is shown in FIG. 1.

An effluent gas stream, 101, from a manufacturing process is combined with recycled unreacted olefin, stream 117, to produce gas mixture stream 102. The effluent gas stream typically contains at least an unreacted olefin, an analogous paraffin, and a third gas.

The third gas is typically methane or an inorganic gas, such as hydrogen, nitrogen or argon. Gases of this type are inevitably present in streams coming from the operations in the manufacturing train, often because they are carried in as unwanted contaminants with the feedstock, and sometime because they are used in the reactors or the product purification steps and have intrinsic value in the manufacturing process if they could be separated and recovered.

The ratio of olefin to paraffin in the stream may be as much as 5:1, 6:1 or even 7:1 or more. If this stream were to be vented from the manufacturing process without further treatment, then as many as five, six, or seven volumes of olefin would be lost for every volume of paraffin that is purged.

Gas mixture stream 102 is routed to compression step, 103, the goal of which is to compress the stream to a pressure which the gas mixture may be partially condensed in the subsequent process steps. The compression step may be carried out using compression equipment of any convenient type, and may be performed in one stage or in a multistage compression train, depending on the degree of compression needed. It is preferred that the pressure to which stream 102 is raised be no more than about 35 bara, and more preferably no more than about 30 bara.

The stream emerging from compression step 103 is compressed stream 104. This stream is sent to a condensation step, 105. The condensation step includes cooling of stream 104 to below the olefin dewpoint temperature, such that a major portion of the olefin is condensed, followed by separation of the resulting liquid and gas phases. Cooling may be performed in any manner, and in one or more sub-steps, including, but not limited to, simple air or water aftercooling of the compressor outlet gases, heat exchange against other on-site process streams, chilling by external refrigerants, and any combinations of these. Preferably, this step should cool stream 104 to a temperature no lower than −40° C., and yet more preferably to no colder than about −35° C.

The liquid and gas phases that are formed by compression and cooling are separated by conventional means in a knock-out drum or the like, 107, to yield condensed liquid stream, 108, and uncondensed gas stream, 114. The condensed liquid stream 108 typically comprises 80 mol %, 90 mol %, or more olefin and paraffin.

Stream 108 is then sent as a feed stream to a membrane separation step, 109. Any membrane with suitable performance properties may be used in this step. The membrane may take the form of a homogeneous film, an integral asymmetric membrane, a multilayer composite membrane, a membrane incorporating a gel or a liquid layer or particulates, or any other form known in the art.

The membrane or membranes to be used in step 109 are made of any material suitable for selectively permeating olefin over paraffin. Preferably, the membranes provide propylene/propane selectivity of at least 5 and propylene flux of 400 gpu under favorable conditions. For ethylene/ethane separation, the preferred selectivity of the membrane is 5 and the preferred ethylene flux is 400 gpu.

These membranes are preferably inorganic membranes. Inorganic membranes with olefin/paraffin separating properties are very finely porous and act as very fine sieves that separate on the basis of polarity difference. Inorganic membranes are characterized by good temperature and chemical resistance. More preferably, the inorganic membranes are zeolite membranes. Such membranes include, but are not limited to, zeolite-based membranes that are crystalline oxides consisting of silicon, aluminum, and other cations, such as sodium and potassium coated on ceramic or other types of support structures.

In some embodiments, membranes for separating olefin and paraffins include polymeric membranes. Typically, these membranes have a selective layer made from a glassy polymer. Representative examples of these membranes include, but are not limited to, poly(phenylene oxide) (PPO), polyimides, perflourinated polyimides, Hyflon® AD, and Cytop®.

In other embodiments, the membranes used in step 109 may include facilitated transport membranes. These contain a liquid that itself contains, for example, free silver ions that react selectively and reversibly with unsaturated hydrocarbons, to selectively carry olefin (propylene) across the membrane.

The membranes may be manufactured as flat sheets or as hollow fibers and housed in any convenient module form, including spiral-wound modules, tubular modules, plate-and-frame modules, and potted hollow-fiber modules. The making of all these types of membranes and modules is well-known in the art.

The membrane separation steps disclosed herein may be carried out using a single membrane module or a bank of membrane modules or an array of modules. A single unit or stage containing on or a bank of membrane modules is adequate for many applications. If either the residue or permeate stream, or both, requires further olefin removal, it may be passed to a second bank of membrane modules for a second processing step. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

The membrane separation steps disclosed herein can be operated by any mechanism that provides a driving force for transmembrane permeation. Most commonly, this driving force is provided by maintaining a pressure difference between the feed and permeate sides, or by sweeping the permeate side continuously with a gas that dilutes the permeating species, both of which techniques are well known in the membrane separation arts.

The membrane separation step, 109, may occur under vapor permeation or pervaporation conditions. By "pervaporation conditions" we mean that the feed is heated to elevate its vapor pressure but maintained at a sufficiently high pressure to prevent evaporation on the feed side of the membrane. The permeate side is maintained at a pressure substantially below the vapor pressure of the feed so vapor will permeate the membrane. If membrane separation step 109 occurs under pervaporation conditions, liquid stream 108 is first heated and then flows to and across the feed side of membrane 110. The low pressure permeate vapor, enriched in the more permeable component, may optionally be cooled and condensed (not shown) or may be compressed and condensed or a combination of the two.

If membrane separation step 109 occurs under vapor permeation conditions, liquid stream 108 is heated and vaporized before flowing across the feed side of membrane 110.

Heating of the liquid stream is shown in further detail in FIG. 3, which is described in more detail below. Liquid stream 108a is heated by direct heater 112 of any convenient type to produce a heated liquid stream 108b, if under pervaporation conditions, or a vaporized stream 108b, if under vapor permeation conditions.

Referring back to FIG. 1, under either condition, a residue stream, 113, that is depleted in olefin relative to stream 108, is withdrawn from the feed side of the membrane. The membrane separation step reduces the olefin content of this stream, preferably to the point that the ratio of olefin to paraffin in the stream is reduced to about 1:1, and more preferably below 1:1. This stream may be purged from the process with comparatively little loss of olefin.

The permeate stream, 111, is enriched in olefin compared with the membrane feed. Optionally, in certain embodiments, this stream may be used as a coolant for heat recovery at various locations within the process to minimize refrigerant energy usage. For example, permeate stream 111 may be used as a coolant in the heat-exchange/condensation step 105, emerging as warmed permeate stream.

Alternatively, if membrane separation step 109 takes place under pervaporation conditions, it may be more beneficial to cool and condense stream 111 to provide or augment the driving force for the pervaporation step.

Permeate stream 111 represents a substantial source of recovered olefin, preferably containing a chemical grade olefin, having an olefin content of at least 90%. In a preferred embodiment, permeate stream 111 is returned as feedstock to the manufacturing reactor. In this case, the permeate stream most preferably contains a polymer grade olefin, having an olefin content of about 99% or above, such as 99.5%.

Uncondensed gas stream, 114, is sent as a feed stream to a second membrane separation step, 115. Prior to this, it may be desirable to heat stream 114 to recover heat and/or to have optimal operating temperatures. Heating of stream 114 may be accomplished by in any way, for example by heat exchange against other on-site process stream or with steam. In FIG. 1, the heat exchange may occur between hot compressed gas stream 104 and cold uncondensed gas stream 114.

The membrane separation step is carried out in a membrane unit containing membrane(s), 116, that are selectively permeable to olefins overs paraffins and inorganic gases. Two options are possible here. The first can be used if it is more important to separate the olefin and paraffin together into the permeate stream, leaving a residue stream that is depleted in all $C_{2+}$ hydrocarbons. For this option, a membrane should be chosen that has good selectivity between the $C_{2+}$ hydrocarbons as a group and the inorganic gases. This may be the situation, for example, if the permeate stream can be passed back to a unit operation where the olefins and paraffins can be separated effectively, or if the inorganic gas is to be purged or vented and should have a low overall hydrocarbon content. In this case, the membranes preferably have a selectivity for $C_{2+}$ hydrocarbons over other gases of at least about 5, more preferably greater than 10, and a hydrocarbon permeance of at least about 400 gpu. The membrane does not need much, if any, selectivity between olefins and paraffins.

Any membrane with suitable performance properties may be used. Typically, for this option, these membranes are polymeric and preferably have a selective layer that comprises a rubbery or elastomeric polymer. Representative preferred membranes include, but are not limited to, nitrile rubber, neoprene, polydimethylsiloxane (silicone rubber), chlorosulfonated polyethylene, polysilicone-carbonate copolymers, and fluoroelastomers. Silicone rubber is the most preferred material for use in this step.

The second option is useful if it is more important to achieve a permeate stream with a high concentration of olefins and relatively little paraffin. A membrane that offers good selectivity between olefin and paraffins in addition to good selectivity between olefins and inorganic gases is needed. In this case, the membrane properties and preferences are similar to those described above with respect to the membrane for step 109.

A driving force for transmembrane permeation is provided by a pressure difference between the feed and permeate sides of the membrane. If the uncondensed gas after the condensation step remains at high pressure, such as above 5 bara, then this is usually adequate to carry out the membrane separation step without additional compression.

Stream 114 flows across the feed side of membrane 116. A residue stream, 118, that is depleted in olefins, and optionally paraffins, relative to stream 114, is withdrawn from the feed side of the membrane. This stream typically contains a high percentage of the third gas, such as nitrogen, hydrogen, or methane and may be sent to any desired destination within or outside of the manufacturing operation, or simply vented or purged. The permeate stream, 117, is enriched in olefins, and optionally paraffins, compared with the membrane feed. Stream 117 is then recycled and combined with effluent gas stream 101 upstream of compression step 103.

Figure 2:
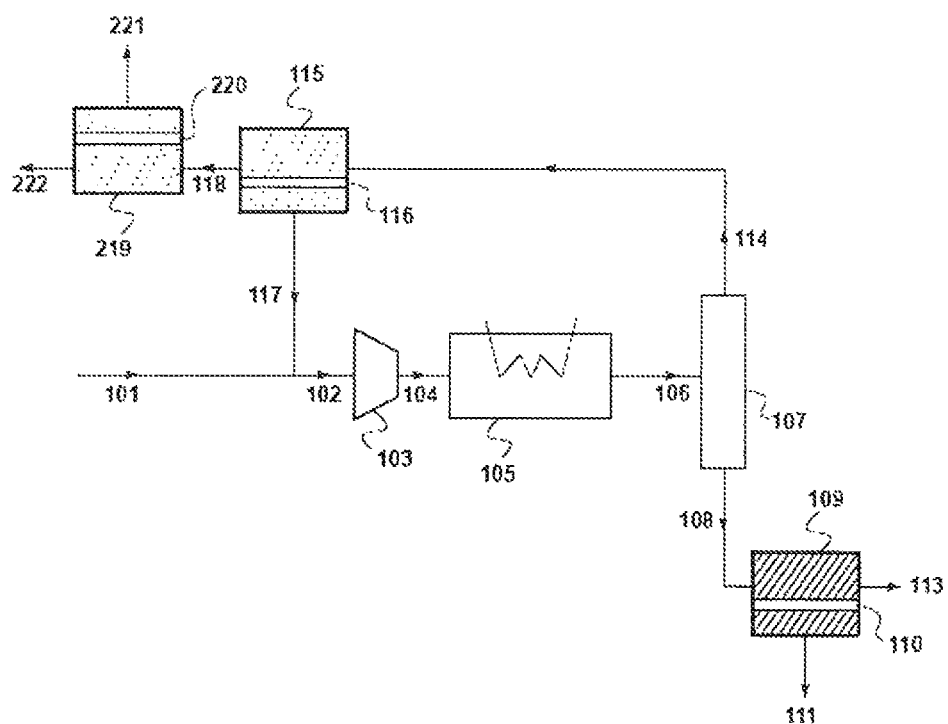
FIG. 2 is a schematic drawing showing a process flow scheme for a variant of the process of FIG. 1, comprising a third membrane separation step.

Another embodiment of the olefin recovery process is shown in FIG. 2. This embodiment is similar to that of FIG. 1 in that the condensed liquid stream 108 and uncondensed gas stream 114 undergo membrane separation.

However, residue stream 118 is now further treated by a third membrane separation step, 219. Stream 118 acts as a feed stream and passes across membrane 220 that is selectively permeable to olefins, and optionally paraffins, over other gases. The residue stream, 222, contains essentially no olefin in this case. The permeate stream, 221, may be sent off to flare or any other suitable destination.

For membrane separation step 219, the preferred membrane materials are similar to the polymeric membranes used in membrane separation step 115, described above.

Figure 3:
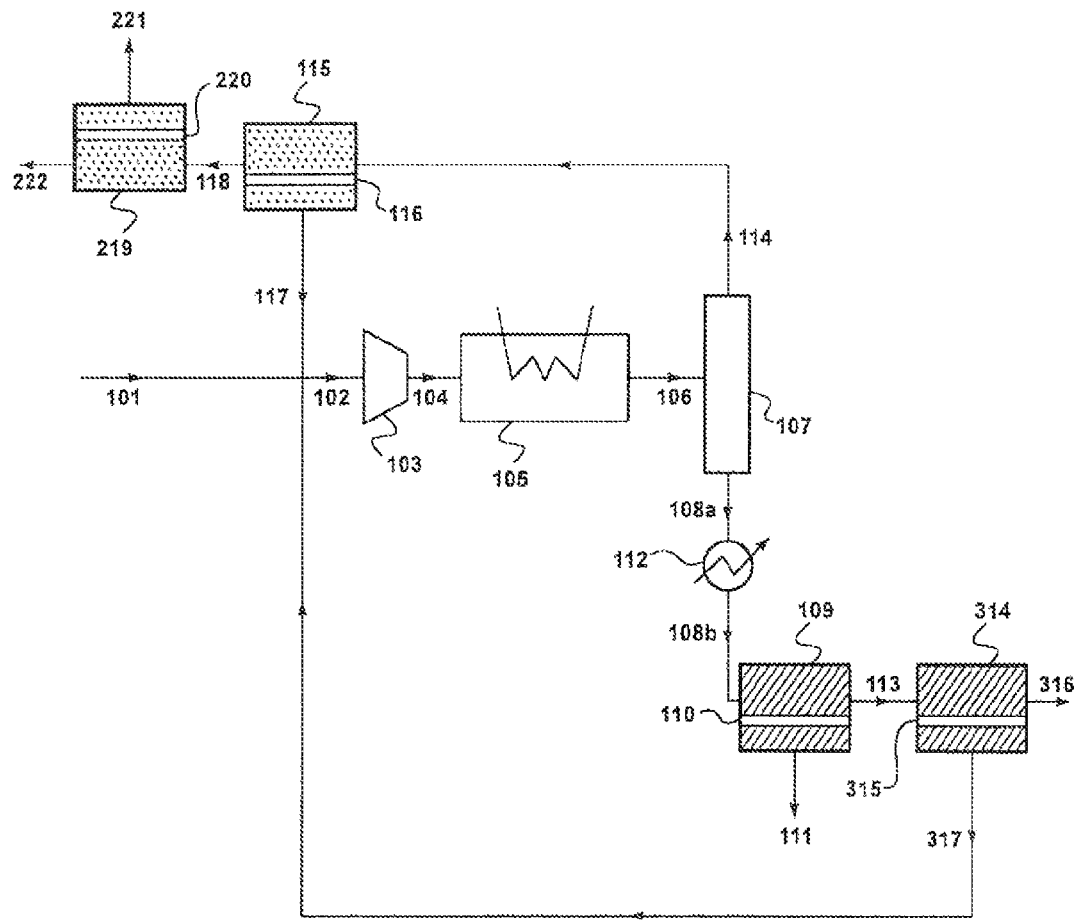
FIG. 3 is a schematic drawing showing a process flow scheme for a variant of the process of FIG. 2, comprising a fourth membrane separation step.

Another embodiment of the olefin recovery process is shown in FIG. 3. This embodiment is similar to that of FIG. 2 in that the condensed liquid stream 108, the uncondensed gas stream 114, and residue stream 118 undergo membrane separation.

In this case, however, residue stream, 113, which is depleted in olefin relative to stream 108, is further treated by a fourth membrane separation step, 314. Stream 113 is passed as a feed stream across membrane 315 that is selectively permeable to olefin over paraffin. The residue stream, 316, contains a major part/most of the paraffin in the effluent gas stream 101 and is purged from the process. The permeate stream, 317, is enriched in olefin and is recycled upstream of compression step 103. In the embodiments of FIGS. 3, 4, 6 and 7, with a suitably high recycle stream 317 or 617, the paraffin content of stream 111 or 512 may be low enough that it can be sent back the manufacturing reactor.

Preferred membranes for membrane separation step 314 are inorganic membranes, similar to those used in membrane separation step 109, described above.

Figure 4:
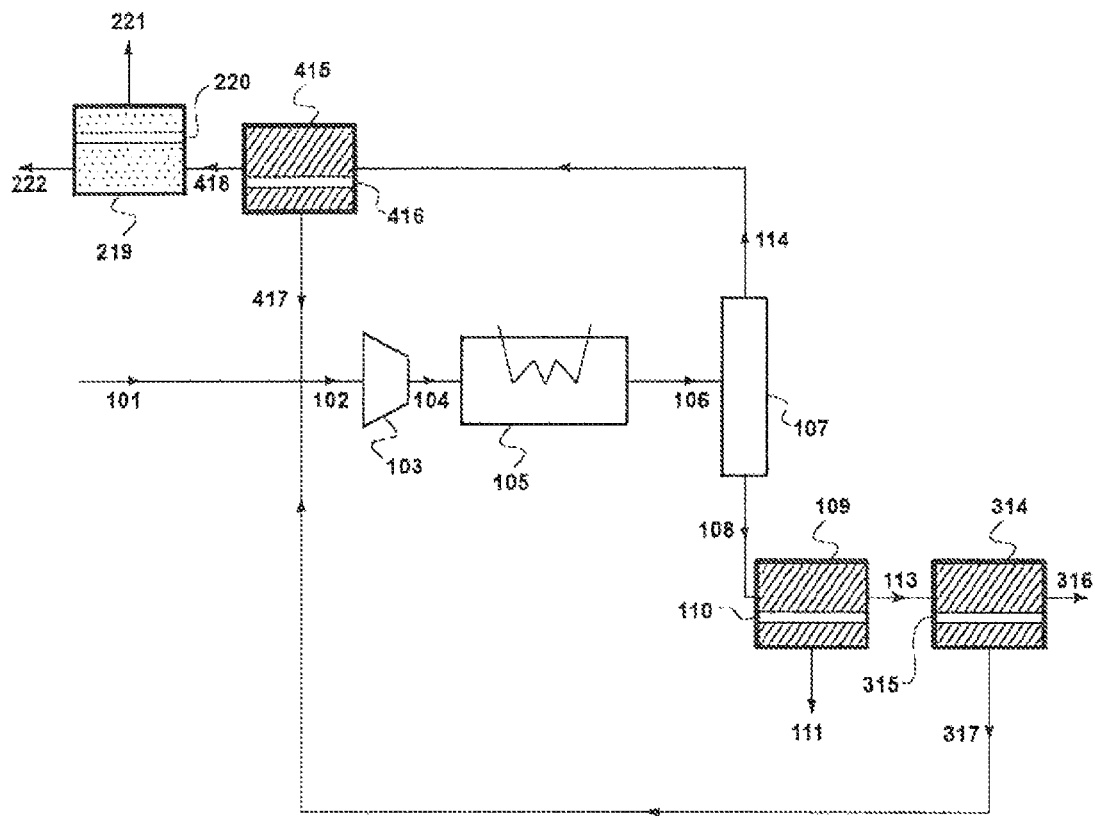
FIG. 4 is a schematic drawing showing a process flow scheme for a variant of the process of FIG. 3, in which the membrane of the second separation step comprises of a different material than that of the membrane in the second separation step in FIG. 3.

Another embodiment of the olefin recovery process is shown in FIG. 4. This embodiment is similar to that of FIG. 3 in that condensed liquid stream 108, first residue stream 113, and uncondensed gas stream 114 undergo membrane separation.

Uncondensed gas stream, 114, is sent as a feed stream to membrane separation step 415. This step is carried out in a membrane unit containing membrane(s), 416, that are selectively permeable to olefin over paraffin and light gases. The membranes preferably are inorganic membranes, similar to those used in membrane separation steps 109 and 314.

Stream 114 flows across the feed side of membrane 416. A residue stream, 418, that is depleted in olefin relative to stream 416, is withdrawn from the feed side of the membrane. While depleted in olefin, this stream comprises paraffin and light gases. Residue stream 418 is then sent to membrane separation step 219 for further treatment as described above. The permeate stream, 417, is enriched in olefin compared with the membrane feed. Stream 417 is recycled and combined with effluent gas stream 101 upstream of compression step 103.

Figure 5:
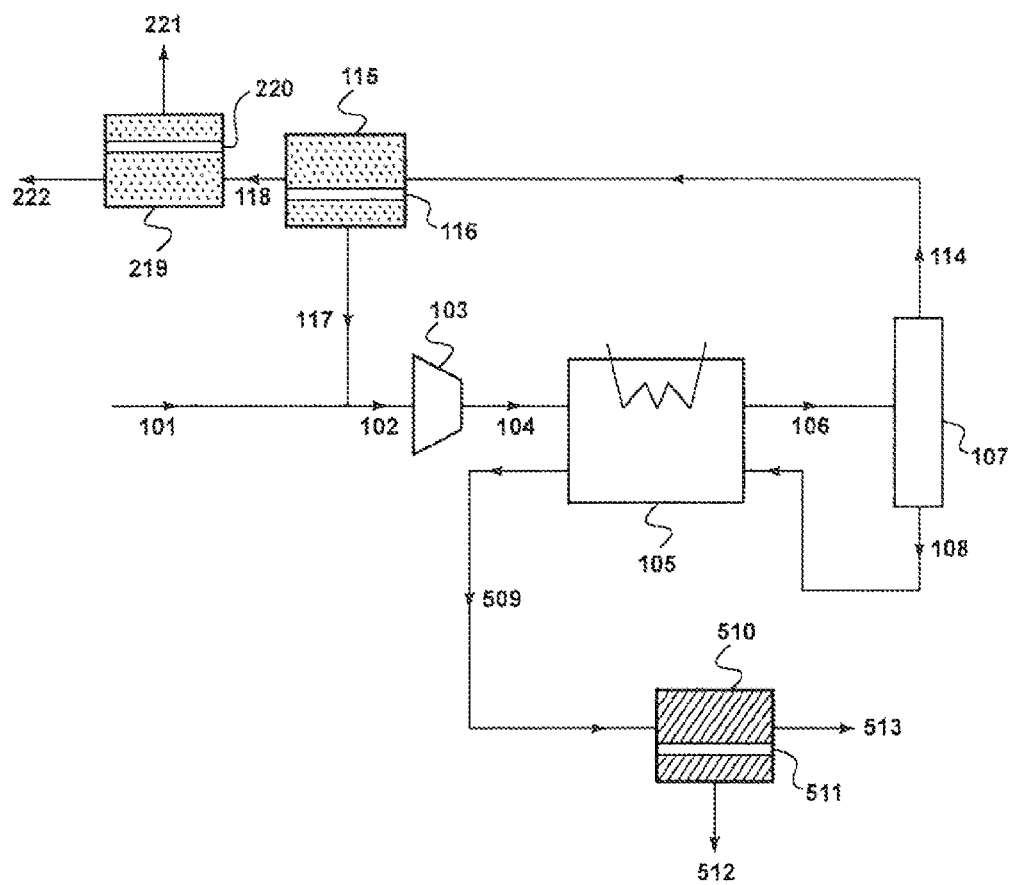
FIG. 5 is a schematic drawing showing a process flow scheme for a variant of the process of FIG. 4, in which the membrane separation step of the condensate is carried out in the vapor phase.

An alternative process configuration to recover unreacted olefin in the effluent gas stream is shown in FIG. 5. This embodiment is similar to that of FIG. 2, except that the condensed liquid stream, 108, is vaporized and the membrane separation step, 510, is carried out in the gas phase. Unless stated otherwise, options and preferences for the various unit operations and streams entering and leaving them in this figure are the same as in the embodiments of FIG. 1-4.

Stream 108 is passed through a heating step where the condensed liquid is vaporized into gas to form stream 509. Heating may be carried out in any way, for example by heat exchange with a suitable hot stream if available on-site, or with steam. In FIG. 5, the heat exchange occurs between hot compressed gas stream 104 and the cold liquid condensate stream 108. In the alternative, stream 108 could be vaporized using a lower temperature heat source by reducing the pressure on the stream by means of a valve or the like.

Vapor stream 509 is then sent as a feed stream to a membrane separation step, 510. This step is carried out in a membrane unit containing membranes, 511, that are selectively permeable to olefin over paraffin. Preferred membranes for this step are similar to those used in membrane separation step 109 in FIG. 1.

Stream 509 flows across the feed side of membrane 511. A residue stream, 513, that is depleted in olefins, but enriched in paraffin relative to stream 509, is withdrawn from the feed side of the membrane and exits the process as a purge gas. Permeate stream 512 is enriched in olefin compared with the membrane feed and may be recycled back to the manufacturing reactor or sent for further processing.

Figure 6:
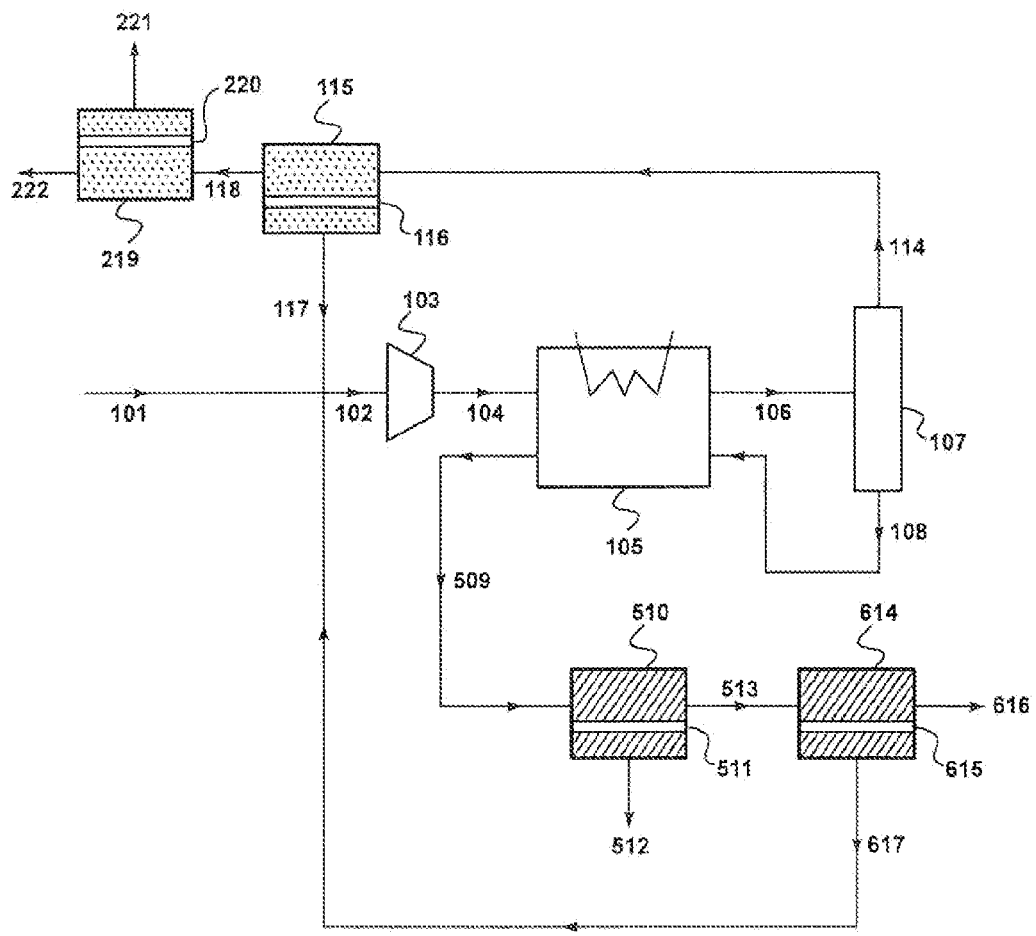
FIG. 6 is a schematic drawing showing a process flow scheme for a variant of the process of FIG. 5, comprising a fourth membrane separation step.

Another embodiment of the olefin recovery process is shown in FIG. 6. This embodiment is similar to that of FIG. 5, but residue stream 513 is further treated with a fourth membrane step.

Residue stream, 513, depleted in olefin relative to stream 509, is further treated by membrane separation step 614. Residue stream 513 is passed as a feed stream across membrane 615 that is selectively permeable to olefin over paraffin. Preferably, these membranes are the same as those used in membrane separation step 510. The residue stream, 616, contains paraffin that is purged from the process. The permeate stream, 617, is enriched in olefin and is recycled upstream of compression step 103.

Figure 7:
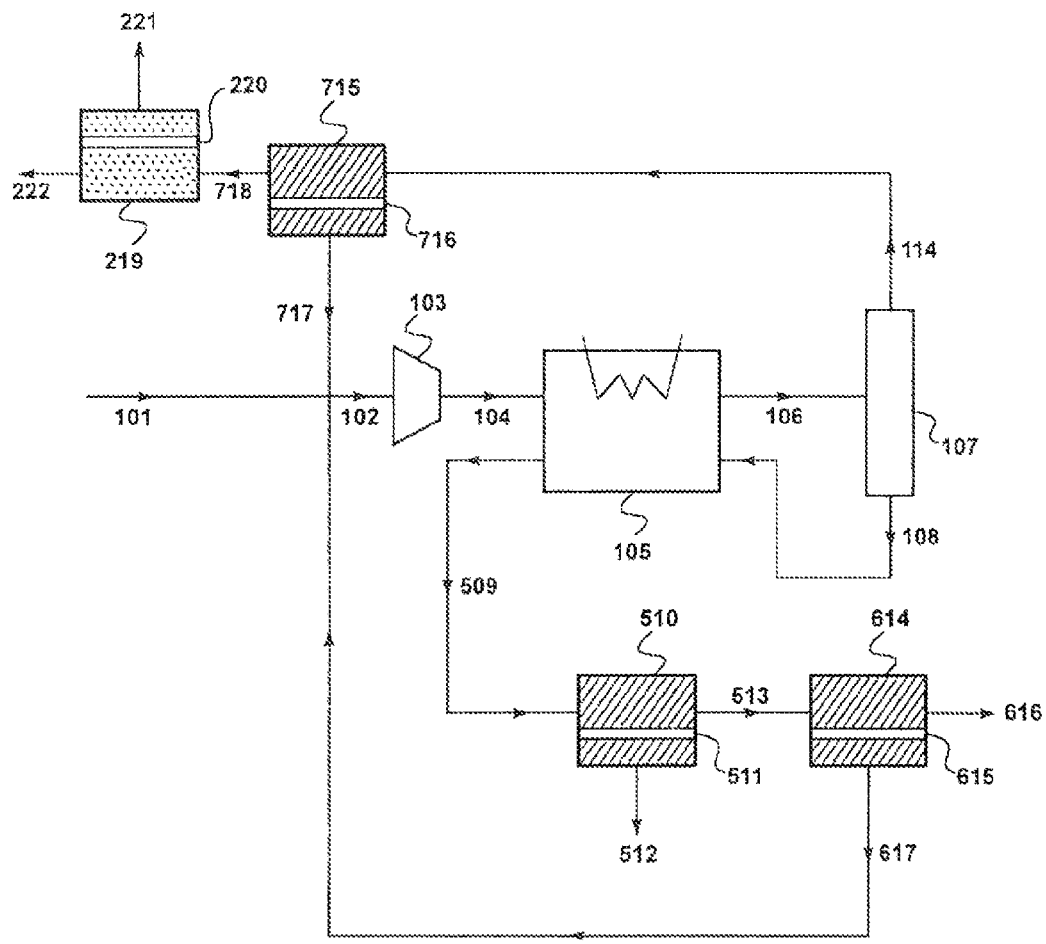
FIG. 7 is a schematic drawing showing a process flow scheme for a variant of the process of FIG. 6, in which the membrane of the second separation step is of a different material than that of the membrane in the second separation step in FIG. 6.

An alternative embodiment to FIG. 6 is shown in FIG. 7. This embodiment is similar to that of FIG. 6, but uncondensed gas stream 114 is treated with a different membrane material.

Uncondensed gas stream, 114, is sent as a feed stream to membrane separation step, 715. This step is carried out in a membrane unit containing membranes, 716, that are selectively permeable to olefins over paraffins as well as olefins over light gases. Preferred membranes are similar to those used in membrane separation steps 510 and 614.

Stream 114 flows across the feed side of membrane 716. A residue stream, 718, that is depleted in olefin relative to stream 114, is withdrawn from the feed side of the membrane and sent to membrane separation step 219 for further treatment. The permeate stream, 717, is enriched in olefin and recycled and combined with purge stream 101 upstream of compression step 103.

Figure 8:
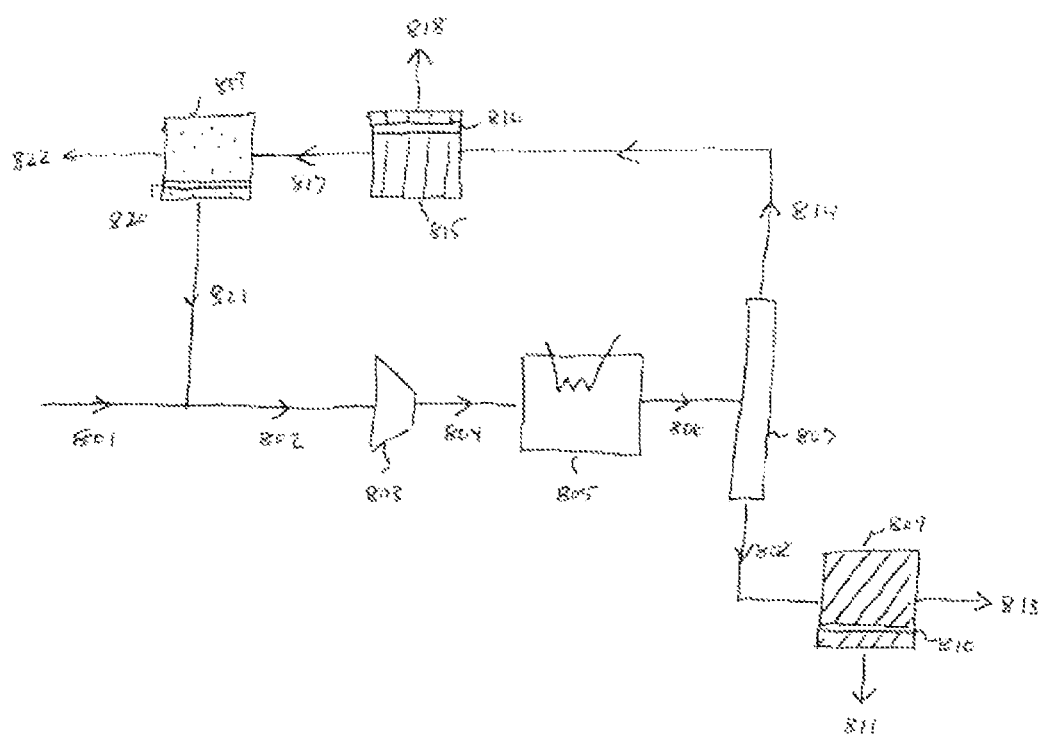
FIG. 8 is a schematic drawing showing an olefin recovery process comprising three membrane separation steps where all three membrane are made of a different material.

Another embodiment of the olefin recovery process is shown in FIG. 8. This embodiment is useful when the effluent stream contains hydrogen, and it is desired to recover some high purity hydrogen from this stream, rather than losing it into the residue stream of step 115 of FIG. 1.

Effluent gas stream, 801, is combined with olefin-enriched permeate stream, 821, to produce gas mixture stream 802. Effluent gas stream 101 typically contains at least an unreacted olefin monomer, a paraffin, and a third gas. In this embodiment, the third gas is hydrogen.

Gas mixture stream 802 is routed to compression step, 803, the goal of which is to compress the stream to a pressure which the gas mixture may be partially condensed in the subsequent process steps. The compression step may be carried out using compression equipment of any convenient type, and may be performed in one stage or in a multistage compression train, depending on the degree of compression needed. It is preferred that the pressure to which stream 802 is raised be no more than about 35 bara, and more preferably no more than about 30 bara.

The stream emerging from compression step 803 is compressed stream 804. This stream is sent to a condensation step, 805. The condensation step includes cooling of stream 804 to below the olefin dewpoint temperature, such that a major portion of the olefin is condensed, followed by separation of the resulting liquid and gas phases. Cooling may be performed in any manner, and in one or more sub-steps, including, but not limited to, simple air or water aftercooling of the compressor outlet gases, heat exchange against other on-site process streams, chilling by external refrigerants, and any combinations of these. Preferably, this step should cool stream 804 to a temperature no lower than −40° C., and yet more preferably to no colder than about −35° C.

The liquid and gas phases that are formed by compression and cooling are separated by conventional means in a knock-out drum or the like, 807, to yield condensed liquid stream, 808, and uncondensed gas stream, 814. The condensed liquid stream 808 typically comprises 80 mol %, 90 mol %, or more olefin and paraffin.

Stream 808 is then sent as a feed stream to a membrane separation step, 809. Any membrane with suitable performance properties may be used in this step. The membrane may take the form of a homogeneous film, an integral asymmetric membrane, a multilayer composite membrane, a membrane incorporating a gel or a liquid layer or particulates, or any other form known in the art.

The membrane or membranes to be used in step 809 are made of any material suitable for selectively permeating olefin over paraffin. Preferably, the membranes provide propylene/propane selectivity of at least 5 and propylene flux of 400 gpu under favorable conditions. For ethylene/ethane separation, the preferred selectivity of the membrane is 5 and the preferred ethylene flux is 400 gpu.

These membranes are preferably inorganic membranes. Inorganic membranes with olefin/paraffin separating properties are very finely porous and act as very fine sieves that separate on the basis of polarity difference. Inorganic membranes are characterized by good temperature and chemical resistance. More preferably, the inorganic membranes are zeolite membranes. Such membranes include, but are not limited to, zeolite-based membranes that are crystalline oxides consisting of silicon, aluminum, and other cations, such as sodium and potassium coated on ceramic or other types of support structures.

The first membrane separation step, 809, may occur under vapor permeation or pervaporation conditions. By "pervaporation conditions" we mean that the feed is heated to elevate its vapor pressure but maintained at a sufficiently high pressure to prevent evaporation on the feed side of the membrane. The permeate side is maintained at a pressure substantially below the vapor pressure of the feed so vapor will permeate the membrane. If membrane separation step 809 occurs under pervaporation conditions, liquid stream 808 is first heated and then flows to and across the feed side of membrane 810. The low pressure permeate vapor, enriched in the more permeable component, may optionally be cooled and condensed (not shown) or may be compressed and condensed or a combination of the two.

If membrane separation step 809 occurs under vapor permeation conditions, liquid stream 808 is heated and vaporized (not shown) before flowing across the feed side of membrane 810.

Under either condition, a residue stream, 813, that is depleted in olefin relative to stream 808, is withdrawn from the feed side of the membrane. The membrane separation step reduces the olefin content of this stream, preferably to the point that the ratio of olefin to paraffin in the stream is reduced to about 1:1, and more preferably below 1:1. This stream may be purged from the process with comparatively little loss of olefin.

The permeate stream, 811, is enriched in olefin compared with the membrane feed. Optionally, in certain embodiments, this stream may be used as a coolant for heat recovery at various locations within the process to minimize refrigerant energy usage. For example, permeate stream 811 may be used as a coolant in the heat-exchange/condensation step 805, emerging as warmed permeate stream.

Alternatively, if membrane separation step 809 takes place under pervaporation conditions, it may be more beneficial to cool and condense stream 811 to provide or augment the driving force for the pervaporation step.

Permeate stream 811 represents a substantial source of recovered olefin, preferably containing a chemical grade olefin, having an olefin content of at least 90%.

Uncondensed gas stream, 814, is sent as a feed stream to a second membrane separation step, 815. Prior to this, it may be desirable to heat stream 814 to recover heat and/or to have optimal operating temperatures. Heating of stream 814 may be accomplished by in any way, for example by heat exchange against other on-site process stream or with steam. In FIG. 8, the heat exchange may occur between hot compressed gas stream 804 and cold uncondensed gas stream 814.

The second membrane separation step, 815, is carried out in a membrane unit containing membrane(s), 816, that are selectively permeable to hydrogen (or any other desired third gas) over $C_{2+}$ hydrocarbons. In this embodiment, the membranes preferably have a selectivity for hydrogen over $C_{2+}$ hydrocarbons and other gases of at least about 10, more preferably greater than 30, and a hydrocarbon permeance of at least about 200 gpu.

Any membrane with suitable performance properties may be used in the second membrane separation step, 815. The membrane may take the form of a homogeneous film, an integral asymmetric membrane, a multilayer composite membrane, a membrane incorporating a gel or liquid layer or particulates, or any other form known in the art.

Representative preferred polymeric membranes have a selective layer based on a polyimide or a polyimide derivative. Other polymeric materials suitable for the selective layer include polybenzimidazole and its derivatives, and polybenzoxazole. Representative materials suitable for inorganic membranes include metals, metal alloys, and ceramics of various types. Yet other suitable membranes include dense ion-transport membranes or proton-conducting membranes.

A driving force for transmembrane permeation is provided by a pressure difference between the feed and permeate sides of the membrane. If the uncondensed gas after the condensation step remains at high pressure, such as above 5 bara, then this is usually adequate to carry out the membrane separation step without additional compression.

Stream 814 flows across the feed side of membrane 816. A residue stream, 817, that is depleted in hydrogen relative to stream 814, is withdrawn from the feed side of the membrane. The permeate stream, 818, is enriched in hydrogen compared with the membrane feed. Preferably, this stream contains 80 mol % or more of hydrogen, and can be a useful source of hydrogen.

Residue stream, 817, depleted in hydrogen compared to stream 814 is further treated by membrane separation step 819. Residue stream 817 is passed as a feed stream across membrane 820 that is selectively permeable to $C_{2+}$ hydrocarbons over other gases. Preferably, these membranes are the same as those used in membrane separation step 115 of FIG. 1. The residue stream, 822, contains waste gases, such as nitrogen or methane. The permeate stream, 821, is enriched in $C_{2+}$ hydrocarbons and is recycled upstream of compression step 803.

Figure 11:
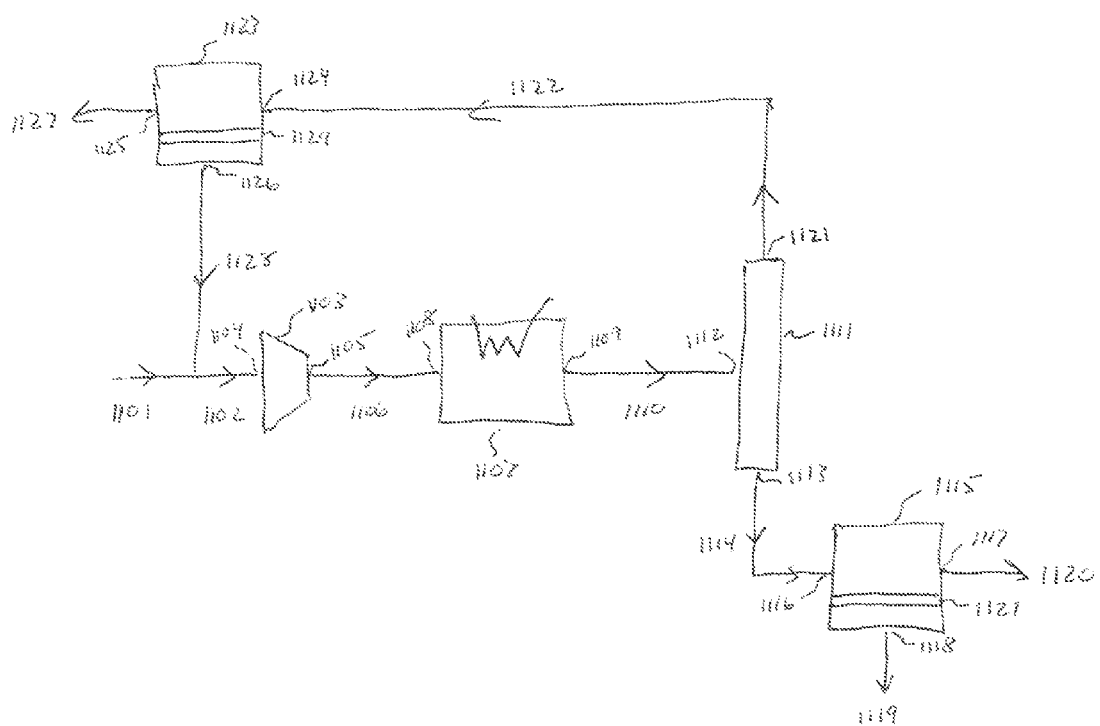
FIG. 11 is a schematic drawing of a basic embodiment of an olefin recovery apparatus that includes a compressor, a condenser, a phase separator, and two membrane separation units.

FIG. 11 is a schematic drawing of an apparatus for recovering olefin in a manufacturing operation. The apparatus comprises a compressor, 1103, that includes an effluent gas inlet, 1104, and a compressed gas outlet, 1105.

In operation, an effluent gas stream, 1101, comprising an olefin, a paraffin, and a third gas, is mixed with a second olefin-enriched stream, 1128, and is introduced into a compressor, 1103, via effluent gas stream inlet, 1104. The compressor, 1103, produces a compressed gas stream, 1106, that exits the compressor through compressed gas outlet, 1105.

The condenser, 1107, comprises a compressed gas inlet, 1108, and a cooled gas outlet, 1110. The compressed gas, 1106, is directed into the compressed gas inlet, 1108, of the condenser where it is cooled to below the olefin dewpoint temperature, such that a major portion of the olefin is condensed. Cooling may be performed in any manner, and may be performed using one or more cooling units, such as heat exchangers, aftercoolers, refrigerators, or any combinations of these. Once cooled, a cooled stream, 1110, exits the condenser through cooled gas outlet, 1110.

The phase separator, 1111, comprises a cooled stream inlet, 1112, a condensed stream outlet, 1113, and an uncondensed stream outlet, 1121. The phase separator, 1111, separates the liquid and gas portions of cooled stream 1110. The cooled stream inlet, 1112, is in fluid communication with cooled stream outlet, 1110. After separation, a condensed stream, 1114, and an uncondensed gas stream, 1122, exit the phase separator, 1111, through outlets 1113 and 1121, respectively.

The first separation unit, 1115, includes a first feed inlet, 1116, a first permeate outlet, 1118, and a first residue outlet, 1117. First separation unit 1115 is in fluid communication with condensed gas stream outlet 1113 of phase separator 1111. The first feed inlet, 1116, allows condensed stream 1114 to enter the first separation unit, 1115. Condensed stream 1114 may enter the first separation unit, 1115, as a liquid or gas depending on the separation conditions.

In embodiments where the separation in first separation unit 1115 occurs under vapor permeation, a vaporizer unit, having a liquid inlet in fluid communication with condensed gas stream outlet 1113 and a gas outlet in gas communication with the first feed inlet, 1116, is used to vaporize the condensed stream.

The condensed stream, 1114, is treated by first separation unit, 1115, which contains membrane 1121 that is selectively permeable to olefin over paraffin. First separation unit 1115 produces a first permeate stream, 1119, and a first residue stream, 1120. The first residue outlet, 1117, and first permeate outlet, 1118, allow for the first residue stream, 1120, and the first permeate stream, 1119, respectively, to be withdrawn from the first separation unit, 1115.

The second separation unit, 1123, includes a second feed inlet, 1124, a second permeate outlet, 1126, and a second residue outlet, 1125. Second separation unit 1123 is in gas communication with the uncondensed gas outlet, 1121, of phase separator 1111. Second feed inlet, 1124, allows the uncondensed gas stream, 1122, to enter the second separation unit, 1123. The uncondensed gas stream is treated by the second separation unit, 1123, which contains a membrane, 1129, that preferentially removes olefins to create a second permeate stream, 1128, and a second residue stream, 1127. Membrane 1129 may alternatively be selectively permeable to $C_{2+}$ hydrocarbons or hydrogen depending on the type of separation to be performed. The second permeate outlet, 1126, and the second residue outlet, 1125, allow for the second permeate stream, 1128, and the second residue stream, 1127, respectively, to be withdrawn from the second separation unit, 1123. The second separation unit, 1123, is also in gas communication with effluent gas stream inlet, 1104, of compressor 1103. This allows the second permeate stream, 1128, to be routed back to the compressor, 1103, for further olefin recovery.

The invention is now further described by the following examples, which are intended to be illustrative of the invention, but are not intended to limit the scope or underlying principles in any way.

EXAMPLES

Example 1

Treatment of the Uncondensed Gas Stream not in Accordance with the Invention

For comparison with the following examples, a calculation was performed in a process where only the uncondensed gas stream 114 from separator 107 was treated. In other words, stream 108 was withdrawn from the separator and was not further treated. The treatment included using two membrane separation steps, similar to steps 115 and 219 in FIG. 2. Likewise, the streams are labeled to correspond with the treatment process of the uncondensed gas stream represented in FIG. 2.

For the calculation, the effluent gas stream was assumed to have a flow rate of 1,139 kg/hour and contain propylene, propane, and nitrogen. It was also assumed that the molar compositions were approximately as follows:
Nitrogen: 76%
Propylene: 21%
Propane: 3%

It was further assumed that the effluent gas stream was compressed to 24 bara in compression step 103, then cooled to −20° C. in condensation step 105.

The calculation was performed using differential element membrane code written at MTR and incorporated into a computer process simulation program (ChemCad 6.3, ChemStations, Austin, Tex.).

The results of the calculations are shown in Table 1:

TABLE 1

| Stream | 101 | 102 | 104 | 106 | 108 | 114 | 117 | 118 | 221 | 222 |
|---|---|---|---|---|---|---|---|---|---|---|
| Total Mass flow (kg/h) | 1,139 | 2,642 | 2,642 | 2,642 | 367 | 2,275 | 1,503 | 772 | 135 | 637 |
| Temp (° C.) | 70 | 46 | 90 | −20 | −20 | −20 | 28 | 22 | 22 | 21 |
| Pressure (bara) | 1 | 1 | 24 | 23 | 23 | 23 | 1 | 23 | 3 | 23 |

TABLE 1-continued

| Stream | 101 | 102 | 104 | 106 | 108 | 114 | 117 | 118 | 221 | 222 |
|---|---|---|---|---|---|---|---|---|---|---|
| Component (mol %) | | | | | | | | | | |
| Nitrogen | 75.9 | 74.6 | 74.6 | 74.6 | 3.7 | 83.0 | 73.7 | 99.0 | 96.9 | 99.5 |
| Propylene | 20.8 | 22.1 | 22.1 | 22.1 | 83.1 | 15.0 | 23.1 | 0.8 | 2.7 | 0.5 |
| Propane | 3.3 | 3.2 | 3.2 | 3.2 | 13.2 | 2.1 | 3.2 | 0.1 | 0.4 | 0.1 |
| Mass flow (kg/h) | | | | | | | | | | |
| Nitrogen | 770 | 1,746 | 1,746 | 1,746 | 9 | 1,737 | 976 | 761 | 129 | 632 |
| Propylene | 317 | 770 | 777 | 777 | 307 | 470 | 461 | 10 | 5 | 4 |
| Propane | 52 | 119 | 119 | 119 | 51 | 68 | 66 | 1 | 1 | 1 |

With only uncondensed gas stream 114 being treated, the process recovers about 640 kg/h of 99.5% purity nitrogen. No olefin depleted in paraffin is recovered.

Example 2

Olefin Recovery Process in Accordance with the Invention of FIG. 3

A calculation was performed to model the performance of the process of FIG. 3 in treating an effluent gas stream in a manufacturing operation. The membrane separation of the liquid condensate occurred under pervaporation conditions.

The results of the calculations are shown in Table 2.

TABLE 2

| Stream | 101 | 108a | 108b | 111 | 113 | 316 | 317 | 114 | 117 | 118 | 221 | 222 |
|---|---|---|---|---|---|---|---|---|---|---|---|---|
| Mass flow (kg/h) | 1,139 | 805 | 805 | 325 | 480 | 43 | 437 | 2,270 | 1,500 | 771 | 135 | 636 |
| Temp (° C.) | 70 | −20 | 40 | 40 | 40 | 38 | 29 | −20 | 28 | 22 | 22 | 21 |
| Pressure (bara) | 1 | 23 | 23 | 1 | 22 | 21 | 1 | 23 | 1 | 3 | 3 | 23 |
| Component (mol %) | | | | | | | | | | | | |
| Nitrogen | 75.9 | 3.8 | 3.8 | 0.5 | 6.0 | 30.0 | 3.4 | 83.2 | 61.2 | 99.0 | 97.0 | 99.5 |
| Propylene | 20.8 | 76.5 | 76.5 | 93.8 | 64.9 | 7.1 | 71.1 | 13.8 | 30.3 | 0.8 | 2.5 | 0.4 |
| Propane | 3.3 | 19.8 | 19.8 | 5.8 | 29.1 | 62.9 | 25.5 | 3.1 | 8.5 | 0.2 | 0.6 | 0.1 |
| Mass flow (kg/h) | | | | | | | | | | | | |
| Nitrogen | 770 | 20 | 20 | 1 | 19 | 9 | 10 | 1,737 | 977 | 760 | 129 | 631 |
| Propylene | 316 | 618 | 618 | 104 | 313 | 3 | 310 | 432 | 424 | 9 | 5 | 4 |
| Propane | 53 | 167 | 167 | 20 | 148 | 31 | 117 | 101 | 99 | 2 | 1 | 1 |

Using polymeric membranes to treat the uncondensed gas stream and inorganic membranes to treat the condensate, the process achieves 96% recovery of olefin. The ratio of olefin to paraffin in purge stream 316 is reduced to about 1:10.

Example 3

Olefin Recovery Process in Accordance with the Invention of FIG. 5

A calculation was performed to model the performance of the process of FIG. 5 in treating an effluent gas stream to recover olefins in a manufacturing operation. The results of the calculations are shown in Table 3.

TABLE 3

| Stream | 101 | 108 | 509 | 512 | 513 | 114 | 117 | 118 | 221 | 222 |
|---|---|---|---|---|---|---|---|---|---|---|
| Mass flow (kg/h) | 1,139 | 367 | 367 | 300 | 68 | 2,275 | 1,503 | 772 | 135 | 637 |
| Temp (° C.) | 70 | −20 | 33 | 31 | 29 | −20 | 28 | 22 | 72 | 21 |
| Pressure (bara) | 1 | 23 | 3 | 1 | 3 | 23 | 1 | 23 | 3 | 23 |
| Component (mol %) | | | | | | | | | | |
| Nitrogen | 75.9 | 3.7 | 3.7 | 0.8 | 16.2 | 83.0 | 73.7 | 99.0 | 96.9 | 99.5 |
| Propylene | 20.8 | 83.1 | 83.1 | 92.9 | 41.0 | 15.0 | 23.1 | 0.8 | 2.7 | 0.4 |
| Propane | 3.3 | 13.2 | 13.2 | 6.2 | 42.8 | 2.1 | 3.2 | 0.1 | 0.4 | 0.1 |
| Mass flow (kg/h) | | | | | | | | | | |
| Nitrogen | 770 | 9 | 9 | 2 | 8 | 1,737 | 976 | 761 | 129 | 632 |
| Propylene | 317 | 307 | 307 | 278 | 29 | 470 | 461 | 10 | 5 | 4 |
| Propane | 52 | 51 | 51 | 20 | 31 | 68 | 66 | 1 | 1 | 1 |

Using polymeric membranes to treat the uncondensed gas stream and an inorganic membrane to treat the condensate, the process achieves 88% recovery of olefin. The ratio of propylene to propane in purge stream 513 is reduced to less than 1:1.

Using polymeric membranes to treat the uncondensed gas stream and inorganic membranes to treat the condensate, the process achieves 96% recovery of olefin. The ratio of olefin to paraffin in purge stream 616 is reduced to about 1:10.

Example 4

Olefin Recovery Process in Accordance with the Invention of FIG. 6

A calculation was performed to model the performance of the process of FIG. 6 in treating an effluent gas stream to recover olefins in a manufacturing operation. The results of the calculations are shown in Table 4.

Example 5

Olefin Recovery Process in Accordance with the Invention of FIG. 7

A calculation was performed to model the performance of the process of FIG. 7 in treating an effluent gas stream to recover olefins in a manufacturing operation. The results of the calculations are shown in Table 5.

TABLE 4

| Stream | 101 | 108 | 509 | 512 | 513 | 616 | 617 | 114 | 117 | 118 | 221 | 222 |
|---|---|---|---|---|---|---|---|---|---|---|---|---|
| Mass flow (kg/h) | 1,139 | 805 | 805 | 325 | 480 | 43 | 437 | 2,270 | 1,500 | 771 | 135 | 636 |
| Temp (° C.) | 70 | −20 | 33 | 32 | 32 | 27 | 29 | −20 | 28 | 22 | 22 | 21 |
| Pressure (bara) | 1 | 23 | 3 | 1 | 3 | 3 | 1 | 23 | 1 | 23 | 3 | 23 |
| Component (mol %) | | | | | | | | | | | | |
| Nitrogen | 75.9 | 3.8 | 3.8 | 0.5 | 6.0 | 30.0 | 3.4 | 83.2 | 61.2 | 99.0 | 97.0 | 99.5 |
| Propylene | 20.8 | 76.5 | 76.5 | 93.8 | 64.9 | 7.1 | 71.1 | 13.8 | 30.3 | 0.8 | 2.5 | 0.4 |
| Propane | 3.3 | 19.8 | 19.8 | 5.8 | 29.1 | 62.9 | 25.5 | 3.1 | 8.5 | 0.2 | 0.6 | 0.1 |
| Mass flow (kg/h) | | | | | | | | | | | | |
| Nitrogen | 770 | 20 | 20 | 1 | 19 | 9 | 10 | 1,737 | 977 | 760 | 129 | 631 |
| Propylene | 316 | 618 | 618 | 304 | 313 | 3 | 310 | 432 | 424 | 9 | 5 | 4 |
| Propane | 53 | 167 | 167 | 20 | 148 | 31 | 117 | 101 | 99 | 2 | 1 | 1 |

TABLE 5

| Stream | 101 | 108 | 509 | 512 | 513 | 616 | 617 | 114 | 717 | 718 | 221 | 222 |
|---|---|---|---|---|---|---|---|---|---|---|---|---|
| Mass flow (kg/h) | 1,142 | 751 | 751 | 329 | 421 | 21 | 400 | 1,383 | 591 | 791 | 219 | 572 |
| Temp (° C.) | 70 | −20 | 33 | 32 | 32 | 27 | 29 | −20 | 29 | 26 | 24 | 24 |
| Pressure (bara) | 1 | 23 | 3 | 1 | 3 | 3 | 1 | 23 | 1 | 23 | 3 | 23 |
| Component (mol %) | | | | | | | | | | | | |
| Nitrogen | 75.9 | 3.8 | 3.8 | 0.5 | 6.3 | 39.3 | 4.4 | 83.1 | 40.5 | 97.7 | 93.9 | 99.1 |
| Propylene | 20.8 | 77.6 | 77.6 | 94.0 | 64.9 | 3.5 | 68.6 | 14.0 | 47.3 | 0.2 | 0.7 | 0.1 |
| Propane | 3.3 | 18.6 | 18.6 | 5.5 | 28.8 | 57.2 | 27.1 | 2.9 | 12.2 | 2.1 | 5.5 | 0.8 |
| Mass flow (kg/h) | | | | | | | | | | | | |
| Nitrogen | 770 | 19 | 19 | 1 | 18 | 6 | 12 | 1,058 | 295 | 763 | 199 | 564 |
| Propylene | 313 | 585 | 585 | 309 | 275 | 1 | 274 | 267 | 264 | 3 | 2 | 1 |
| Propane | 59 | 147 | 147 | 19 | 128 | 14 | 114 | 58 | 32 | 25 | 18 | 7 |

Using the combination of a polymeric membrane and an inorganic membrane to treat the uncondensed gas stream and inorganic membranes to treat the condensate, the process achieves almost 99% recovery of olefin at 94% purity. The ratio of olefin to paraffin in purge stream 616 is reduced to 1:14.

Example 6

Olefin Recovery Process in Accordance with the Invention of FIG. 7

Figure 9:
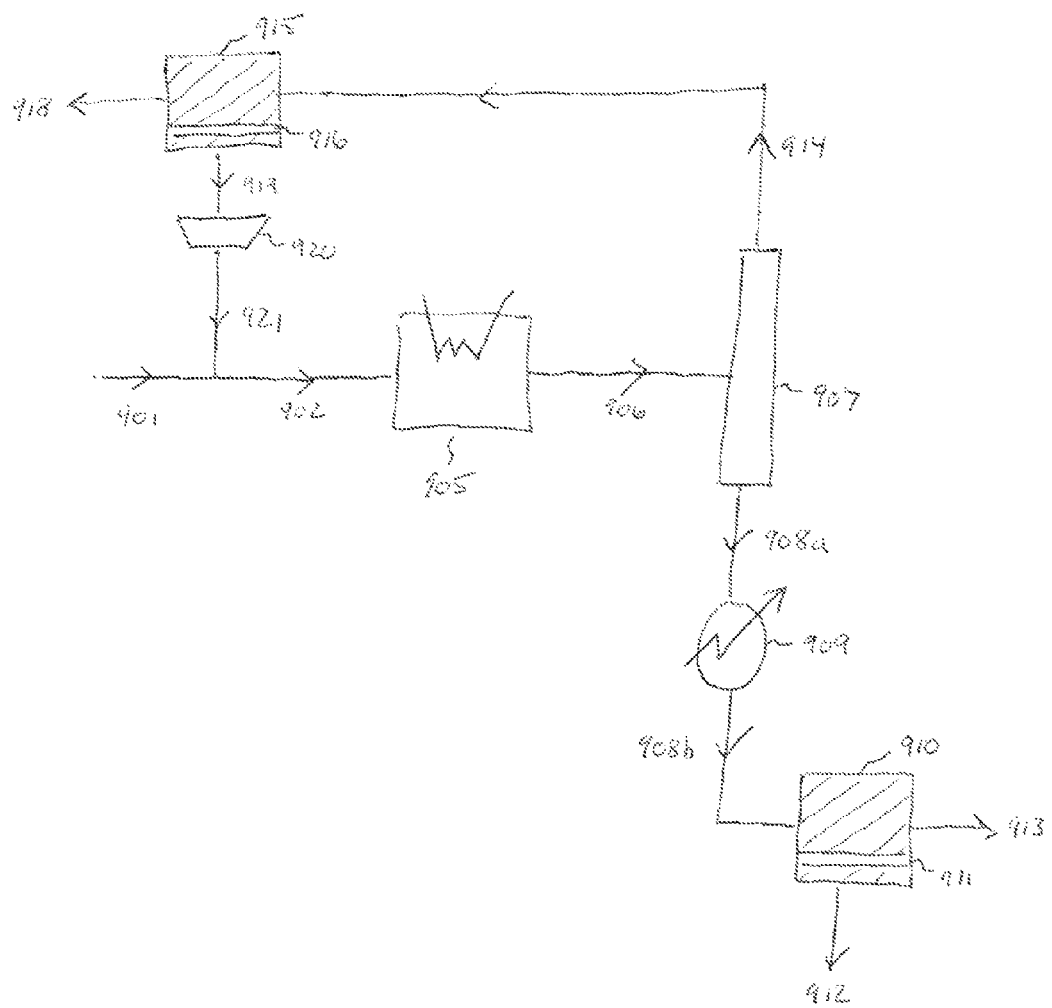
FIG. 9 is a schematic drawing showing an olefin recovery process where the source of the effluent gas stream is from a steam cracker and the process comprises a first membrane and a second membrane that are made of the same material.

A calculation was performed to model the performance of the process of FIG. 9 in treating an effluent gas stream to recover olefins in a manufacturing operation. All assumptions regarding stream composition and operating conditions were the same as in Example 5 unless otherwise stated. Recycle rates, membrane operating pressures and membrane areas are selected to recover propylene at a higher purity than previous examples.

TABLE 6

| Stream | 101 | 108 | 509 | 512 | 513 | 616 | 617 | 114 | 717 | 718 | 221 | 222 |
|---|---|---|---|---|---|---|---|---|---|---|---|---|
| Mass flow (kg/h) | 1,142 | 4,670 | 4,670 | 236 | 4,434 | 210 | 4,224 | 1,286 | 605 | 682 | 201 | 480 |
| Temp (° C.) | 70 | −20 | 50 | 50 | 50 | 40 | 40 | −20 | 29 | 25 | 24 | 23 |
| Pressure (bara) | 1 | 23 | 23 | 3 | 23 | 23 | 4 | 23 | 1 | 23 | 3 | 3 |
| Component (mol %) | | | | | | | | | | | | |
| Nitrogen | 75.9 | 3.6 | 3.6 | 0.2 | 3.8 | 54.3 | 0.8 | 82.7 | 59.9 | 99.6 | 99.0 | 99.9 |
| Propylene | 20.8 | 94.6 | 94.6 | 99.6 | 94.3 | 27.1 | 98.4 | 17.0 | 39.7 | 0.2 | 0.5 | 0.1 |
| Propane | 3.3 | 1.8 | 1.8 | 0.2 | 1.9 | 18.5 | 0.8 | 0.3 | 0.4 | 0.2 | 0.5 | 0.1 |
| Mass flow (kg/h) | | | | | | | | | | | | |
| Nitrogen | 770 | 115 | 115 | 1 | 115 | 92 | 22 | 979 | 301 | 678 | 198 | 479 |

TABLE 6-continued

| Stream | 101 | 108 | 509 | 512 | 513 | 616 | 617 | 114 | 717 | 718 | 221 | 222 |
|---|---|---|---|---|---|---|---|---|---|---|---|---|
| Propylene | 313 | 4,468 | 4,468 | 235 | 4,233 | 69 | 4,164 | 302 | 300 | 2 | 1 | 1 |
| Propane | 59 | 88 | 88 | 1 | 87 | 49 | 38 | 5 | 3 | 2 | 2 | 1 |

Using the combination of a polymeric membrane and an inorganic membrane to treat the uncondensed gas stream and inorganic membranes to treat the condensate, the process achieves 75% recovery of olefin at 99.6% purity. The ratio of olefin to paraffin in purge stream 616 is reduced to 1:0.7.

Example 7

Olefin Recovery Process in Accordance with the Invention of FIG. 9

A calculation was performed to model the performance of the process of FIG. 9 in treating an effluent gas stream to recover olefins in a steam cracking operation. For the calculation, the effluent gas stream was assumed to have a flow rate of 13,943 kg/hour and contain propylene, propane, hydrogen, nitrogen, methane, ethylene, ethane, and $C_{4+}$ hydrocarbons. It was also assumed that the molar compositions were approximately as follows:
Hydrogen: 28%
Methane: 22%
Ethylene: 19%
Propylene: 13%
Ethane: 10%
Nitrogen: 5%
Propane: 2%
$C_{4+}$: 1%

It was further assumed that the effluent gas stream was cooled to −20° C. in condensation step 905.

The calculation was performed using differential element membrane code written at MTR and incorporated into a computer process simulation program (ChemCad 6.3, ChemStations, Austin, Tex.).

Referring to FIG. 9, an effluent gas stream, 901, is combined with a compressed gas stream, 921, to form a mixed gas stream, 902. Gas stream 901 is at a high enough pressure coming from the steam cracker that no compression is needed. Thus, the mixed gas stream, 902, can be sent directly to a condensation step, 905. The condensation step includes cooling of stream 902 to below the olefin dewpoint temperature, such that a major portion of the olefin is condensed, followed by separation of the resulting liquid and gas phases.

The liquid and gas phases that are formed by compression and cooling are separated by conventional means in a knockout drum or the like, 907, to yield condensed liquid stream, 908a, and uncondensed gas stream, 914.

Condensed liquid stream 908a is heated by direct heater, 909, of any convenient type to produce a vapor stream 908b. In the alternative, stream 908a could be vaporized using a lower temperature heat source by reducing the pressure on the stream by means of a valve or the like. In some embodiments, the cold condensed liquid stream 908a may be heated by heat exchange with the hot compressed gas stream, 904.

Vapor stream 908b is then passed as a feed stream to a first membrane separation step, 910. Membrane or membranes, 911, to be used in step 910 are inorganic membranes, but any other material suitable for selectively permeating olefin over paraffin may be used. A first residue stream, 913, that is depleted in olefin relative to stream 908b, is withdrawn from the feed side of the membrane. This stream may be purged from the process with comparatively little loss of olefin. A first permeate stream, 912, enriched in olefin compared to stream 909, is withdrawn from the permeate side of the membrane and may be recycled back to the manufacturing reactor or sent for further processing.

First membrane separation step 910 reduces the olefin content of stream 913, preferably to the point that the ratio of olefin to paraffin in the stream is reduced to about 1:1, and more preferably below 1:1.

Uncondensed gas stream, 914, is sent as a feed stream to a second membrane separation step, 915. Prior to this, it may be desirable to heat stream 914 (not shown) to recover heat and/or to have optimal operating temperatures. Heating of stream 914 may be accomplished by in any way, for example by heat exchange against other on-site process stream or with steam.

Second membrane separation step 915 is carried out in a membrane unit containing membrane(s), 916, which are made of an inorganic material, but any other suitable material may be used that selectively permeates olefin over paraffin and other light gases.

Uncondensed gas stream 914 flows across the feed side of second membrane 916. A second residue stream, 918, that is depleted in olefin relative to stream 914, is withdrawn from the feed side of the membrane. A second permeate stream, 919, is enriched in olefin compared with the membrane feed.

The permeate stream, 919, may be recycled back to the process by sending this stream to compressor 920 to produce a compressed gas stream, 921. Stream 921 is then recycled upstream of condensation step 905.

The results of the calculations are shown in Table 7:

TABLE 7

| Stream | 901 | 902 | 906 | 914 | 919 | 918 | 908b | 912 | 913 |
|---|---|---|---|---|---|---|---|---|---|
| Mass flow (kg/h) | 13,943 | 41,992 | 41,986 | 36,223 | 28,050 | 8,174 | 5,762 | 5,216 | 546 |
| Temp (° C.) | 54 | 64 | −20 | 80 | 75 | 69 | 80 | 69 | 58 |
| Pressure (bara) | 15 | 15 | 15 | 15 | 1 | 15 | 15 | 1 | 15 |

TABLE 7-continued

| Stream | 901 | 902 | 906 | 914 | 919 | 918 | 908b | 912 | 913 |
|---|---|---|---|---|---|---|---|---|---|
| Component (mole %) | | | | | | | | | |
| Methane | 22 | 11 | 11 | 12 | 4 | 28 | 2 | 1 | 13 |
| Ethane | 10 | 8 | 8 | 8 | 7 | 10 | 9 | 7 | 28 |
| Ethylene | 19 | 46 | 46 | 47 | 65 | 15 | 31 | 33 | 14 |
| Propane | 2 | 1 | 1 | 1 | 0 | 2 | 4 | 2 | 23 |
| Propylene | 13 | 17 | 17 | 14 | 21 | 1 | 51 | 56 | 4 |
| $C_{4+}$ hydrocarbons | 1 | 0 | 0 | 0 | 0 | 0 | 3 | 2 | 14 |
| Hydrogen | 28 | 13 | 13 | 14 | 2 | 36 | 0 | 0 | 2 |
| Nitrogen | 5 | 2 | 2 | 2 | 0 | 6 | 0 | 0 | 1 |
| Mass flow (kg/h) | | | | | | | | | |
| Methane | 2,359 | 2,921 | 2,921 | 2,876 | 562 | 2,314 | 45 | 11 | 34 |
| Ethane | 1,986 | 4,015 | 4,015 | 3,605 | 2,029 | 1,577 | 410 | 277 | 133 |
| Ethylene | 3,524 | 20,536 | 20,529 | 19,141 | 17,012 | 2,130 | 1,388 | 1,328 | 61 |
| Propane | 670 | 874 | 874 | 587 | 204 | 383 | 287 | 126 | 161 |
| Propylene | 3,672 | 11,727 | 11,725 | 8,366 | 8,054 | 312 | 3,359 | 3,333 | 26 |
| $C_{4+}$ hydrocarbons | 355 | 409 | 409 | 145 | 54 | 91 | 264 | 137 | 127 |
| Hydrogen | 376 | 419 | 420 | 419 | 44 | 375 | 1 | 0 | 1 |
| Nitrogen | 926 | 968 | 968 | 963 | 42 | 921 | 5 | 0 | 5 |

Using inorganic membranes to treat the uncondensed gas stream and the condensate, the process achieves 91% recovery of olefin. The ratio of olefin to paraffin in purge stream 913 is reduced to 1:6.

Example 8

Figure 10:
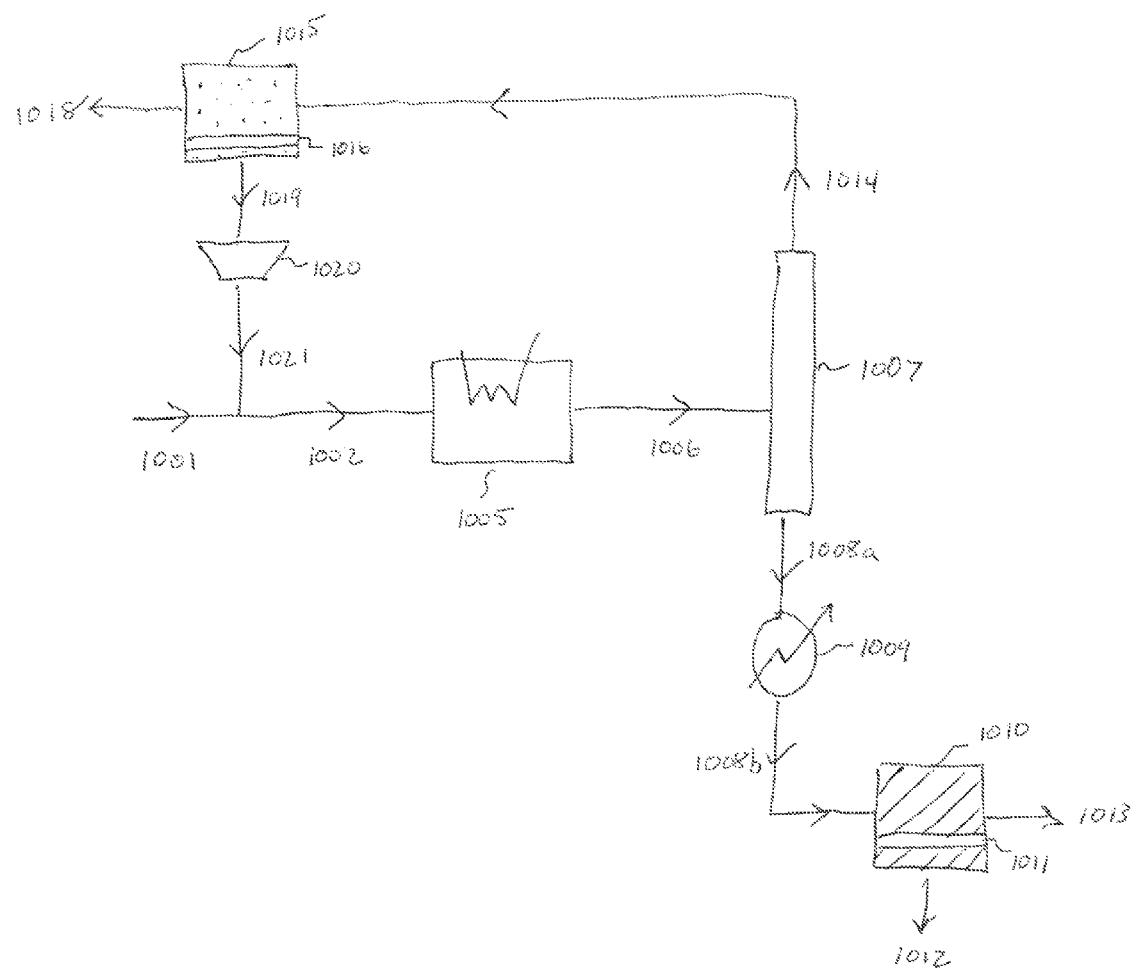
FIG. 10 is a schematic drawing showing an olefin recovery process where the source of the effluent gas stream is from a butanol production operation and the process comprises a first membrane and a second membrane that are made of a different material.

Olefin Recovery Process in Accordance with the Invention of FIG. 10

A calculation was performed to model the performance of the process of FIG. 10 in treating an effluent gas stream to recover olefins in a butanol manufacturing operation. For the calculation, the effluent gas stream was assumed to have a flow rate of 908 kg/hour and contain propylene, propane, nitrogen, hydrogen, methane, carbon monoxide, n-butyraldehyde, carbon dioxide, and argon. It was also assumed that the molar compositions were approximately as follows:
Propylene: 27%
Propane: 26%
Nitrogen: 18%
Hydrogen: 15%
Methane: 5%
Carbon Monoxide: 3%
n-Butyraldehyde: 2%
Carbon Dioxide: 2%
Argon: 2%

It was further assumed that the effluent gas stream was cooled to −20° C. in condensation step 1005.

The calculation was performed using differential element membrane code written at MTR and incorporated into a computer process simulation program (ChemCad 6.3, ChemStations, Austin, Tex.).

Referring to FIG. 10, an effluent gas stream, 1001, is combined with a compressed gas stream, 1021, to form a mixed gas stream, 1002. Gas stream 1001 is at a high enough pressure coming from the non-polymeric olefin derivative manufacturing operation that no compression is needed. Thus, the mixed gas stream, 1002, can be sent directly to a condensation step, 1005. The condensation step includes cooling of stream 1002 to below the olefin dewpoint temperature, such that a major portion of the olefin is condensed, followed by separation of the resulting liquid and gas phases.

The liquid and gas phases that are formed by compression and cooling are separated by conventional means in a knock-out drum or the like, 1007, to yield condensed liquid stream, 1008a, and uncondensed gas stream, 1014.

Condensed liquid stream 1008a is heated by direct heater, 1009, of any convenient type to produce a vapor stream 1008b. In the alternative, stream 1008a could be vaporized using a lower temperature heat source by reducing the pressure on the stream by means of a valve or the like. In some embodiments, the cold condensed liquid stream 1008a may be heated by heat exchange with the hot compressed gas stream, 1004.

Vapor stream 1008b is then passed as a feed stream to a first membrane separation step, 1010. Membrane or membranes, 1011, to be used in step 1010 are inorganic membranes, but any other material suitable for selectively permeating olefin over paraffin may be used. A first residue stream, 1013, that is depleted in olefin relative to stream 1008b, is withdrawn from the feed side of the membrane. This stream may be purged from the process with comparatively little loss of olefin. A first permeate stream, 1012, enriched in olefin compared to stream 1009, is withdrawn from the permeate side of the membrane and may be recycled back to the manufacturing reactor or sent for further processing.

First membrane separation step 1010 reduces the olefin content of stream 1013, preferably to the point that the ratio of olefin to paraffin in the stream is reduced to about 1:1, and more preferably below 1:1.

Uncondensed gas stream, 1014, is sent as a feed stream to a second membrane separation step, 1015. Prior to this, it may be desirable to heat stream 1014 (not shown) to recover heat and/or to have optimal operating temperatures. Heating of stream 1014 may be accomplished by in any way, for example by heat exchange against other on-site process stream or with steam.

Second membrane separation step 1015 is carried out in a membrane unit containing membrane(s), 1016, made with any suitable material that selectively permeates $C_{2+}$ hydrocarbons over inorganic gases.

Uncondensed gas stream 1014 flows across the feed side of second membrane 1016. A second residue stream, 1018, that is depleted in olefin relative to stream 1014, is withdrawn from the feed side of the membrane. A second permeate stream, 1019, is enriched in olefin compared with the membrane feed.

The permeate stream, 1019, may be recycled back to the process by sending this stream to compressor 1020 to produce a compressed gas stream, 1021. Stream 1021 is then recycled upstream of condensation step 1005.

The results of the calculations are shown in Table 8:

TABLE 8

| Stream | 1001 | 1002 | 1006 | 1014 | 1019 | 1018 | 1008a | 1008b | 1012 | 1013 |
|---|---|---|---|---|---|---|---|---|---|---|
| Mass flow (kg/h) | 908 | 1,793 | 1,794 | 1,100 | 884 | 216 | 694 | 694 | 423 | 271 |
| Temp (° C.) | 44 | 42 | −20 | −20 | 31 | 27 | −20 | 80 | 74 | 69 |
| Pressure (bara) | 14 | 14 | 14 | 14 | 1 | 14 | 14 | 13 | 1 | 13 |
| Component (mole %) | | | | | | | | | | |
| Hydrogen | 15 | 23 | 23 | 30 | 29 | 36 | 0 | 0 | 0 | 1 |
| Argon | 2 | 2 | 2 | 3 | 3 | 3 | 0 | 0 | 0 | 1 |
| Nitrogen | 18 | 15 | 15 | 19 | 12 | 42 | 1 | 1 | 0 | 2 |
| Methane | 5 | 11 | 11 | 14 | 15 | 9 | 2 | 2 | 1 | 3 |
| Carbon Monoxide | 3 | 5 | 5 | 7 | 7 | 8 | 0 | 0 | 0 | 1 |
| Propane | 26 | 18 | 18 | 10 | 13 | 1 | 45 | 45 | 20 | 81 |
| Propylene | 27 | 20 | 20 | 12 | 16 | 1 | 46 | 46 | 69 | 10 |
| Carbon Dioxide | 2 | 4 | 4 | 4 | 6 | 0 | 3 | 3 | 5 | 0 |
| N-Butyraldehyde | 2 | 1 | 1 | 0 | 0 | 0 | 4 | 4 | 5 | 2 |
| Mass flow (kg/h) | | | | | | | | | | |
| Hydrogen | 9 | 30 | 30 | 30 | 21 | 9 | 0 | 0 | 0 | 0 |
| Argon | 17 | 60 | 60 | 59 | 43 | 16 | 1 | 1 | 0 | 1 |
| Nitrogen | 141 | 265 | 266 | 263 | 125 | 138 | 3 | 3 | 0 | 3 |
| Methane | 22 | 113 | 113 | 109 | 91 | 18 | 4 | 4 | 1 | 3 |
| Carbon Monoxide | 26 | 95 | 95 | 94 | 69 | 25 | 1 | 1 | 0 | 1 |
| Propane | 318 | 521 | 521 | 207 | 203 | 4 | 314 | 314 | 86 | 227 |
| Propylene | 312 | 554 | 555 | 248 | 243 | 5 | 307 | 307 | 281 | 26 |
| Carbon Dioxide | 23 | 113 | 113 | 91 | 90 | 1 | 22 | 22 | 21 | 1 |
| N-Butyraldehyde | 41 | 41 | 41 | 0 | 0 | 0 | 41 | 41 | 33 | 7 |

Using inorganic membranes to treat the uncondensed gas stream and the condensate, the process achieves 90% recovery of olefin. The ratio of olefin to paraffin in purge stream 1013 is reduced to about 1:9.

I claim:

1. A process for treating an effluent gas stream arising from an operation that manufactures an olefin, said effluent gas stream comprising an olefin, a paraffin and a third gas, the process comprising the steps of:
    (a) passing the effluent gas stream to a compressor to produce a compressed stream;
    (b) partially condensing the compressed stream, including cooling and separating the compressed stream into a condensed liquid condensate enriched in olefin and paraffin and an uncondensed gas stream depleted in olefin and paraffin;
    (c) separating the condensed liquid condensate from step (b) using a first membrane to produce a first olefin-enriched permeate stream and a first olefin-depleted residue stream;
    (d) separating the uncondensed gas stream from step (b) using a second membrane to produce a second olefin-enriched permeate stream and a second olefin-depleted residue stream; and
    (e) returning the second olefin-enriched permeate stream upstream of the compressor.

2. The process of claim 1, wherein the olefin is selected from the group consisting of ethylene, propylene and butylene.

3. The process of claim 1, wherein the operation is selected from the group consisting of steam cracking, fluid catalytic cracking, propane dehydrogenation, olefin metathesis, a methanol-to-olefin process, and a methanol-to-propylene process.

4. The process of claim 3, wherein the operation is steam cracking.

5. The process of claim 3, wherein the operation is fluid catalytic cracking.

6. The process of claim 1, wherein the first membrane is an inorganic membrane.

7. The process of claim 1, wherein the second membrane is a polymeric membrane.

8. The process of claim 1, wherein the second olefin-enriched permeate stream is enriched in paraffin compared to the uncondensed gas stream.

9. The process of claim 1, wherein the second olefin-enriched permeate stream is depleted in paraffin compared to the uncondensed gas stream.

10. The process of claim 1, further comprising the step of:
(f) separating the second olefin-depleted residue stream using a third membrane to produce a third olefin-enriched permeate stream and a third olefin-depleted residue stream.

11. The process of claim 1, further comprising the steps of:
(g) separating the first olefin-depleted residue stream using a fourth membrane to produce a fourth olefin-enriched permeate stream and a fourth olefin-depleted residue stream; and
(h) returning the fourth olefin-enriched permeate stream upstream of the compressor.

12. The process of claim 11, wherein the fourth membrane is an inorganic membrane.

13. The process of claim 1, wherein the condensed liquid condensate is revaporized prior to step (c).

14. The process of claim 1, wherein the third gas is nitrogen or hydrogen.

15. The process of claim 1, wherein the uncondensed gas stream from step (b) is separated using a second membrane to produce a hydrogen-enriched permeate stream and a hydrogen-depleted residue stream.

16. The process of claim 15, wherein the hydrogen-depleted residue is separated using a third membrane to produce a hydrocarbon-enriched permeate stream and a hydrocarbon-depleted residue stream and the hydrocarbon-enriched residue stream is returned upstream of the compressor.

17. A process for treating an effluent gas stream arising from an operation that manufactures a non-polymeric olefin derivative, said effluent gas stream comprising an olefin, a paraffin and a third gas, the process comprising the steps of:
(a) passing the effluent gas stream to a compressor to produce a compressed stream;
(b) partially condensing the compressed stream, including cooling and separating the compressed stream into a condensed liquid condensate enriched in olefin and paraffin and an uncondensed gas stream depleted in olefin and paraffin;
(c) separating the condensed liquid condensate from step (b) using a first membrane to produce a first olefin-enriched permeate stream and a first olefin-depleted residue stream;
(d) separating the uncondensed gas stream from step (b) using a second membrane to produce a second olefin-enriched permeate stream and a second olefin-depleted residue stream; and
(e) returning the second olefin-enriched permeate stream upstream of the compressor.

18. The process of claim 17, wherein the olefin is selected from the group consisting of ethylene, propylene and butylene.

19. The process of claim 17, wherein the operation is selected from the group consisting of chlorohydrin production, butyraldehyde, oxo alcohol production, isopropyl alcohol production, acrylic acid production, allyl chloride production, acrylonitrile production, cumene production, ethylene oxide production, vinyl acetate production, ethylene dichloride production, ethanol production, and ethylbenzene production.

20. The process of claim 19, wherein the olefin manufacturing operation is acrylonitrile production.

21. The process of claim 19, wherein the olefin manufacturing operation is ethylene oxide production.

22. The process of claim 17, wherein the first membrane is an inorganic membrane.

23. The process of claim 17, wherein the second membrane is a polymeric membrane.

24. The process of claim 17, wherein the second olefin-enriched permeate stream is enriched in paraffin compared to the uncondensed gas stream.

25. The process of claim 17, wherein the second olefin-enriched permeate stream is depleted in paraffin compared to the uncondensed gas stream.

26. The process of claim 17, further comprising the step of:
(f) separating the second olefin-depleted residue stream using a third membrane to produce a third olefin-enriched permeate stream and a third olefin-depleted residue stream.

27. The process of claim 26, further comprising the steps of:
(g) separating the first olefin-depleted residue stream using a fourth membrane to produce a fourth olefin-enriched permeate stream and a fourth olefin-depleted residue stream; and
(h) returning the fourth olefin-enriched permeate stream upstream of the compressor.

28. The process of claim 27, wherein the fourth membrane is an inorganic membrane.

29. The process of claim 17, wherein the condensed liquid condensate is revaporized prior to step (c).

30. The process of claim 17, wherein the third gas is a non-polymeric olefin-derivative.

31. The process of claim 30, wherein the non-polymeric olefin-derivative is selected from the group consisting of chlorohydrin, butyraldehyde, oxo alcohol, isopropyl alcohol, acrylic acid, allyl chloride, acrylonitrile, cumene, ethylene oxide, vinyl acetate, ethylene dichloride, ethanol, and ethylbenzene.

32. A process for treating an effluent gas stream arising from an operation that manufactures an olefin, said effluent gas stream comprising an olefin, a paraffin and a third gas, the process comprising the steps of:
(a) partially condensing the effluent gas stream, including cooling and separating the effluent gas stream into a condensed liquid condensate enriched in olefin and paraffin and an uncondensed gas stream depleted in olefin and paraffin;
(b) separating the condensed liquid condensate from step (a) using a first membrane to produce a first olefin-enriched permeate stream and a first olefin-depleted residue stream;
(c) separating the uncondensed gas stream from step (a) using a second membrane to produce a second olefin-enriched permeate stream and a second olefin-depleted residue stream;
(d) passing the second olefin-enriched permeate stream to a compressor to produce a compressed stream; and
(e) returning the compressed stream upstream of step (a).

33. A process for treating an effluent gas stream arising from an operation that manufactures a non-polymeric olefin derivative, said effluent gas stream comprising an olefin, a paraffin and a third gas, the process comprising the steps of:
(a) partially condensing the effluent gas stream, including cooling and separating the effluent gas stream into a condensed liquid condensate enriched in olefin and paraffin and an uncondensed gas stream depleted in olefin and paraffin;
(b) separating the condensed liquid condensate from step (a) using a first membrane to produce a first olefin-enriched permeate stream and a first olefin-depleted residue stream;

(c) separating the uncondensed gas stream from step (a) using a second membrane to produce a second olefin-enriched permeate stream and a second olefin-depleted residue stream;
(d) passing the second olefin-enriched permeate stream to a compressor to produce a compressed stream; and
(e) returning the compressed stream upstream of step (a).

* * * * *